(12) United States Patent  
Fujii et al.

(10) Patent No.: US 9,895,124 B2
(45) Date of Patent: Feb. 20, 2018

(54) X-RAY CT APPARATUS AND IMAGE RECONSTRUCTION METHOD

(71) Applicant: HITACHI, LTD., Tokyo (JP)

(72) Inventors: Hideaki Fujii, Tokyo (JP); Tetsuo Nakazawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 198 days.

(21) Appl. No.: 14/905,057

(22) PCT Filed: Jul. 24, 2014

(86) PCT No.: PCT/JP2014/069505
§ 371 (c)(1),
(2) Date: Jan. 14, 2016

(87) PCT Pub. No.: WO2015/012331
PCT Pub. Date: Jan. 29, 2015

(65) Prior Publication Data
US 2016/0183900 A1  Jun. 30, 2016

(30) Foreign Application Priority Data

Jul. 26, 2013 (JP) ................................. 2013-155600

(51) Int. Cl.
*H01J 35/30* (2006.01)
*A61B 6/00* (2006.01)
(Continued)

(52) U.S. Cl.
CPC ............ *A61B 6/5205* (2013.01); *A61B 6/032* (2013.01); *A61B 6/4021* (2013.01);
(Continued)

(58) Field of Classification Search
CPC ......... A61B 6/032; A61B 6/03; A61B 6/5205; G01N 2223/419; G01N 23/046
(Continued)

(56) References Cited

U.S. PATENT DOCUMENTS

2004/0081279 A1   4/2004  Brunnett
2009/0185655 A1*  7/2009  Koken ................... A61B 6/032
                                                    378/11
2012/0069950 A1   3/2012  Grasruck et al.

FOREIGN PATENT DOCUMENTS

JP   2006503631 A   2/2006
JP   2011229906 A   11/2011
JP   2013085956 A   5/2013

* cited by examiner

Primary Examiner — Don Wong

(57) ABSTRACT

In an FFS method that improves spatial resolution by moving an X-ray focal spot to multiple positions to acquire projection data, in order to provide an X-ray CT apparatus and an image reconstruction method that enables to improve spatial resolution of the entire effective field of view without reducing a rotational speed, the X-ray focal spot in the X-ray tube device 101 is shifted to acquire focal shift projection data (FFS projection data), the virtual view generation unit 126 up-samples the FFS projection data (generates a virtual view) in the view direction, and the reconstruction computing unit 127 reconstructs an image using actual data of the FFS projection data in the central region 604 closer to the image center than a predetermined boundary and using the up-sampled projection data in the peripheral region 603 outside the boundary in an image reconstruction computing process.

11 Claims, 25 Drawing Sheets

(51) Int. Cl.
*A61B 6/03* (2006.01)
*G06T 11/00* (2006.01)
*G06T 3/40* (2006.01)

(52) U.S. Cl.
CPC .......... *A61B 6/4435* (2013.01); *G06T 3/4069* (2013.01); *G06T 11/005* (2013.01); *G06T 11/006* (2013.01); *A61B 6/465* (2013.01); *A61B 6/467* (2013.01); *A61B 6/469* (2013.01)

(58) Field of Classification Search
USPC ...................................... 378/4, 901, 11, 154
See application file for complete search history.

FIG.12
(a)
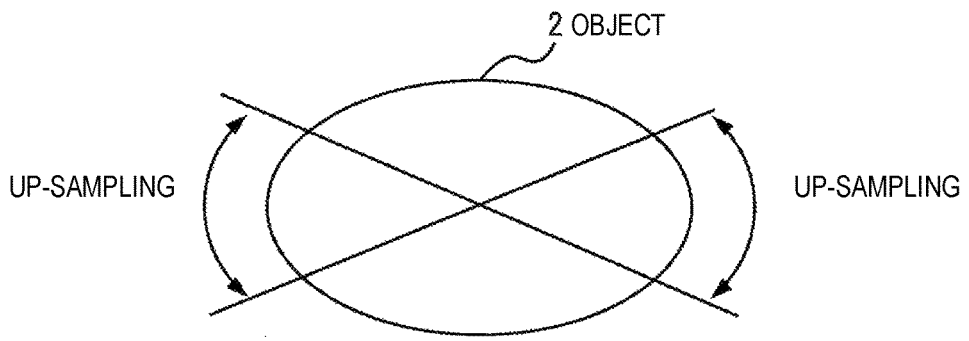
(b)
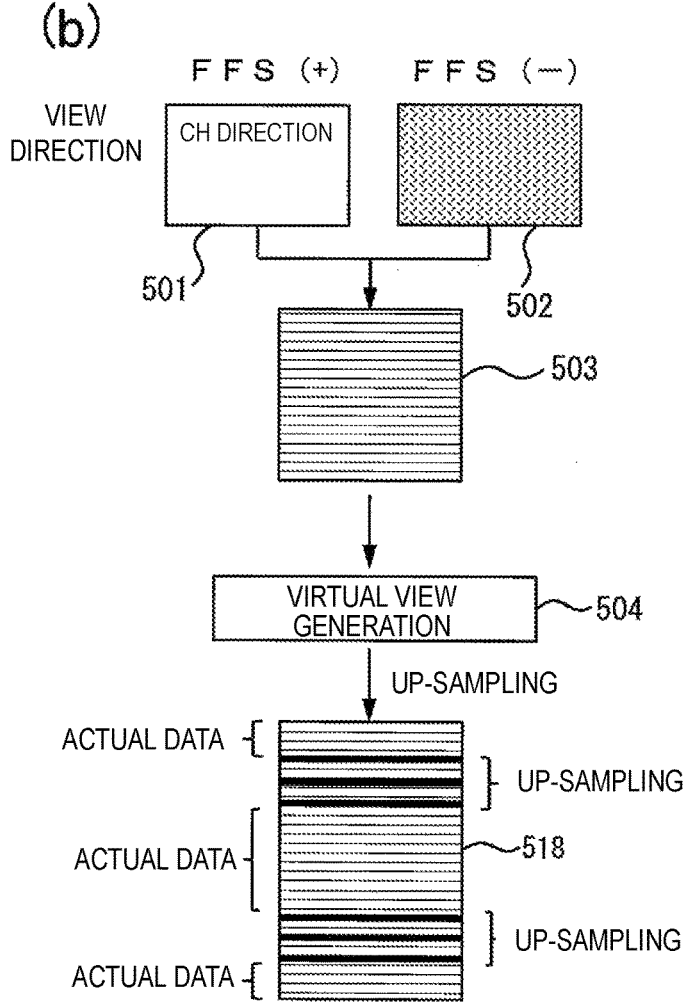

FIG.21
(a)
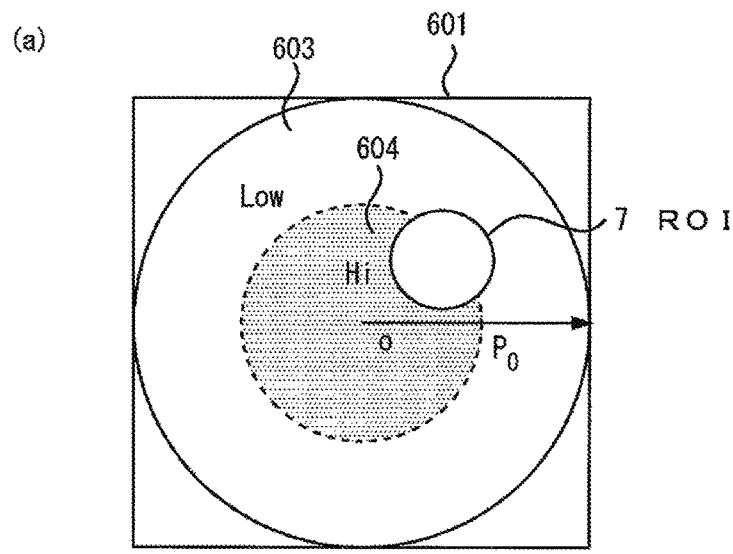
(b)
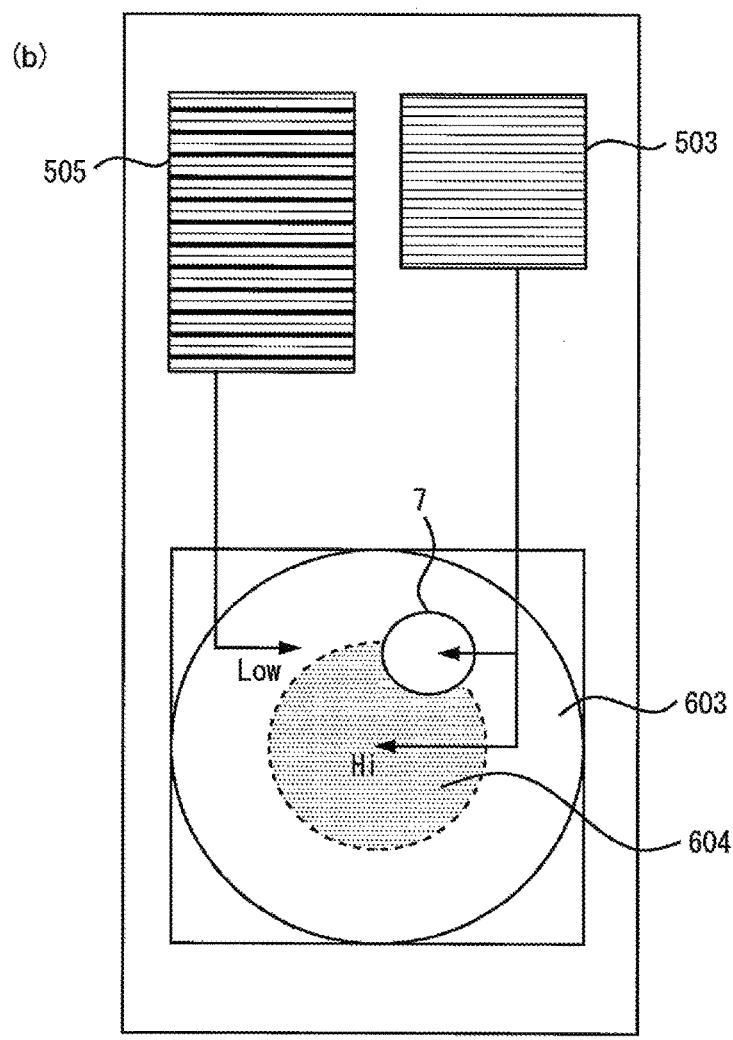

$$\xi(V) = \xi(V1) + \xi(V2) + \xi(V3)$$

$\xi(V) = W(V1)\xi(V1) + W(V2)\xi(V2) + W(V3)\xi(V3)$ $$\xi(V) = W(V1)\xi(V1) + W(V2)\xi(V2) + W(V3)\xi(V3) + \cdots + W(Vn)\xi(Vn)$$

X-RAY CT APPARATUS AND IMAGE RECONSTRUCTION METHOD

TECHNICAL FIELD

The present invention relates to an X-ray CT apparatus and an image reconstruction method, and in detail, to an image reconstruction method suitable for an X-ray CT apparatus using an X-ray tube device that can irradiate X-rays from a plurality of focal spots.

BACKGROUND ART

An X-ray CT apparatus is an apparatus in which an X-ray tube device and an X-ray detector are oppositely disposed to rotate around an object, irradiates X-rays from a plurality of rotation angle directions (views) to detect the X-ray transmitted through the object for each view, and generate a tomographic image of the object based on the detected projection data. In the recent years, an FFS (Flying Focal Spot) X-ray tube device having a function to irradiate X-rays to a plurality of spots by shifting an X-ray focus has been developed. In the FFS X-ray tube device, an X-ray focal spot can be shifted to a plurality of positions by electromagnetically moving a position of an electronic beam entering the anode (target). Hence, a plurality of projection data whose X-ray irradiation paths are different can be acquired from the same rotation angle direction (view), which can improve spatial resolution of the X-ray CT apparatus (the FFS method).

By the way, there is a problem that spatial resolution around the center of the entire effective field of view is improved while the spatial resolution deteriorates in the peripheral portion other than the central portion in an image reconstructed using the conventional FFS method. On the contrary to this, a BFFS (Balanced Flying Focus Spot) method is suggested in the patent literature 1, which homogenizes and improves the spatial resolution of the peripheral portion by setting an optimal focal movement distance based on the number of views to be scanned during one rotation (an angle difference between adjacent views) and a distance between the X-ray tube device and the rotational center.

CITATION LIST

Patent Literature

PTL 1: Japanese Unexamined Patent Publication No. 2010-35812

SUMMARY OF INVENTION

Technical Problem

However, a sampling rate and a gantry rotation speed of a data collection device are limited due to hardware limitations. Therefore, in order to increase the number of views to be scanned during one rotation, the gantry rotation speed needs to be reduced. When the number of views is increased by reducing the rotational speed, motion artifacts are adversely increased in case of a fast-moving organ such as the heart. The faster movement of the organ such as the heart, the more such motion artifacts affect an image considerably, which is inconvenient for a radiologist performing image diagnosis. Therefore, there is a request to improve spatial resolution over the entire effective field of view without reducing the rotational speed in scanning a moving site as a target.

The present invention was made in view of the above problems, and the purpose is to provide an X-ray CT apparatus and an image reconstruction method that can improve spatial resolution of the entire effective field of view without reducing a rotational speed in the FFS method for improving spatial resolution by moving an X-ray focal spot to a plurality of positions to acquire projection data.

Solution to Problem

In order to achieve the above purpose, the first invention is an X-ray CT apparatus characterized by comprising an X-ray tube device for irradiating X-rays to an object from a plurality of focal spots, an X-ray detector disposed oppositely to the X-ray tube device for detecting transmission X-rays transmitted through the object, a rotary disk that is equipped with the X-ray tube device and the X-ray detector and rotates around the object, a focal shift X-ray controller for shifting the focal spot in the X-ray tube device to arbitrary positions, a focal shift projection data generation unit for generating focal shift projection data in combination with the transmission X-rays by each of the irradiated X-rays whose focal spots were shifted to a plurality of positions by the focal shift X-ray controller, a virtual view generation unit for generating a virtual view in the view direction of the focal shift projection data to generate up-sampled projection data using the virtual view, and a reconstruction computing unit for reconstructing an image using actual data of the focal shift projection data in the central region closer to the image center than a predetermined boundary in the image plane and using the up-sampled projection data in the peripheral region outside the boundary.

The second invention is an image reconstruction method characterized by including the steps of acquiring focal shift projection data that is projection data by each of the irradiated X-rays of which focal spot was shifted to a plurality of positions in the X-ray tube device, generating a virtual view in the view direction of the focal shift projection data to generate up-sampled projection data using the virtual view, and reconstructing an image using actual data of the focal shift projection data in the central region closer to the image center than a predetermined boundary in the image plane and using the up-sampled projection data in the peripheral region outside the boundary.

Advantageous Effects of Invention

The present invention can provide an X-ray CT apparatus and an image reconstruction method that can improve spatial resolution of the entire effective field of view without reducing a rotational speed in the FFS method for improving spatial resolution by moving an X-ray focal spot to a plurality of positions to acquire projection data.

BRIEF DESCRIPTION OF DRAWINGS

FIG. 12 is a diagram explaining the up-sampled projection data 518 that is partially different in the number of views.

FIG. 21 is a schematic diagram explaining an ROI set in the reconstruction computing process of the fourth embodiment and projection data to be used for each region.

DESCRIPTION OF EMBODIMENTS

Hereinafter, referring to the attached diagrams, suitable embodiments of the present invention will be described in detail.

First Embodiment

First, referring to FIG. 1, the overall configuration of the X-ray CT apparatus 1 will be described.

Figure 1:
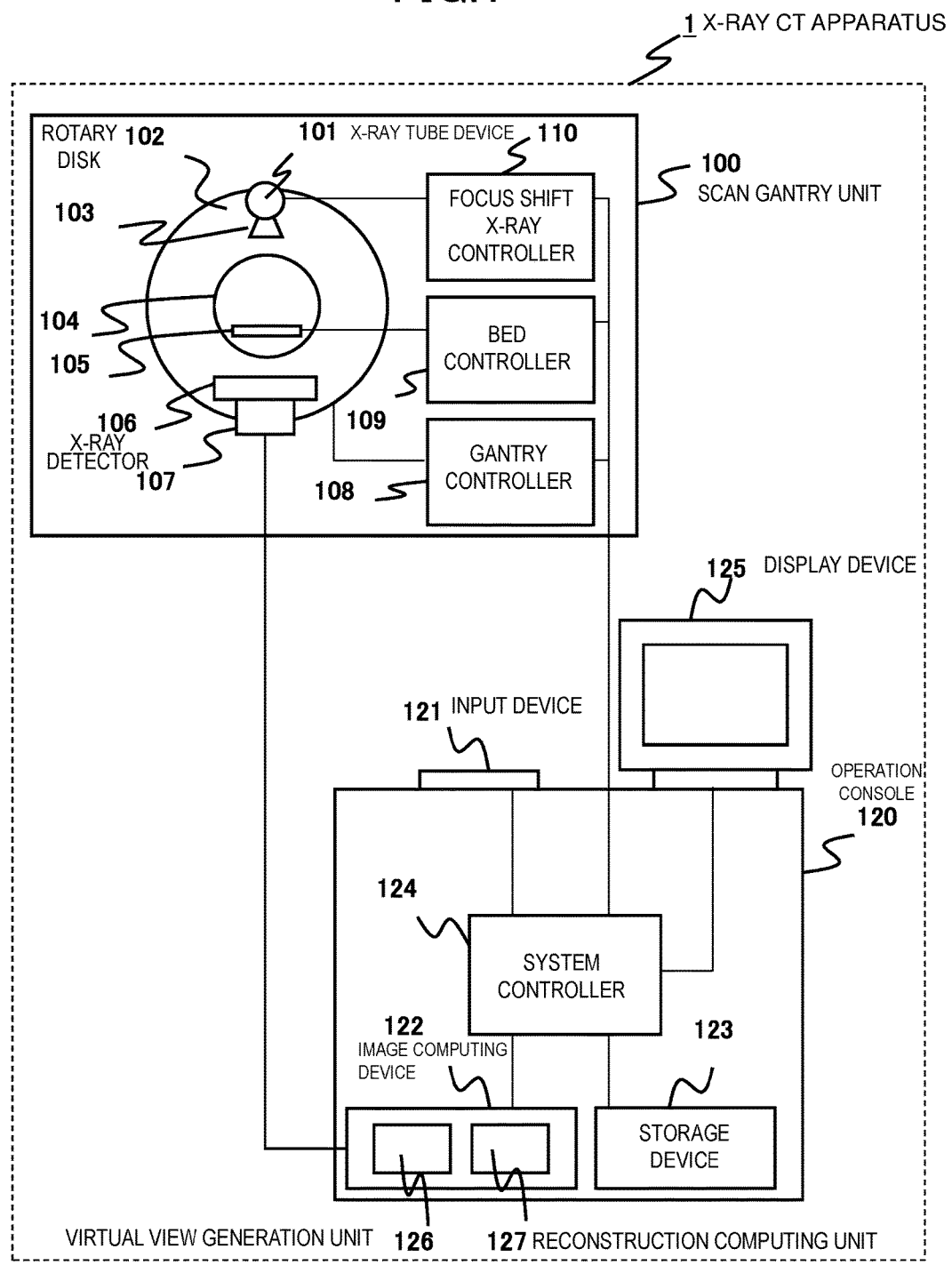
FIG. 1 is an overall configuration diagram of the X-ray CT apparatus 1.

As shown in FIG. 1, the X-ray CT apparatus 1 is provided with the scan gantry unit 100 and the operation console 120.

The scan gantry unit 100 is a device for irradiating an X-ray to an object and detecting the X-ray transmitted through the object and is comprised of the X-ray tube device 101, the rotary disk 102, the collimator 103, the X-ray detector 106, the data collection device 107, the gantry controller 108, the bed controller 109, and the focal shift X-ray controller 110.

The rotary disk 102 is provided with the opening 104, and the X-ray tube device 101 and the X-ray detector 106 are disposed oppositely across the opening 104. An object placed on the bed 105 is inserted in the opening 104. The rotary disk 102 rotates around the object using the driving force to be transmitted through the driving transmission system from the rotary disk driving device controlled by the gantry controller 108.

The operation console 120 is a device for controlling each part of the scan gantry unit 100 and acquiring projection data measured in the scan gantry unit 100 to generate and display an image. The operation console 120 is provided with the input device 121, the image computing device 122, the storage device 123, the system controller 124, and the display device 125.

The X-ray tube device 101 is a flying focus X-ray tube device that can move a focal spot in the rotating anode (target). When the rotation axis direction of the X-ray CT apparatus 1 is set to the Z direction, the flying focus X-ray tube device deflects an electronic beam to be irradiated to the rotating anode (target) to the X or Y direction orthogonal to the Z direction. Hence, an X-ray focal spot is shifted, and X-rays of minutely different paths are irradiated from the same view position.

In the present embodiment, a focus moving direction by the X-ray tube device 101 is set to the rotation direction (channel direction) of the X-ray CT apparatus 1. Also, the focal spots are set to spots shifted by "+σa" and "−σb" in the rotation direction (channel direction) from the reference focal spot. That is, the X-ray tube device 101 irradiates X-rays respectively from the first focal spot "+σa" moved in the positive direction of the channel direction and the second focal spot "−σb" moved in the negative direction.

In the following description, projection data acquired using the FFS (Flying Focus Spot) method is referred to as FFS projection data. Particularly, projection data acquired using an X-ray irradiated from the above first focal spot is referred to as FFS (+) projection data, and projection data acquired using an X-ray irradiated from the above second focal spot is referred to as FFS (−) projection data. Also, projection data acquired using an X-ray irradiated from the reference focal spot without the FFS technique is referred to as FFS (without) projection data.

The X-ray tube device 101 is controlled by the focal shift X-ray controller 110 and continuously or intermittently irradiates an X-ray of a predetermined intensity. The focal shift X-ray controller 110 controls an X-ray tube voltage and an X-ray tube current to be applied or supplied to the X-ray tube device 101 according to the X-ray tube voltage and the X-ray tube current determined by the system controller 124 of the operation console 120. The focal shift X-ray controller 110 controls alternate movement to the above first and second focal spots for each view according to the rotation of the rotary disk 102 for example.

The X-ray irradiation port of the X-ray tube device 101 is provided with the collimator 103. The collimator 103 restricts an irradiation range of an X-ray emitted from the X-ray tube device 101. For example, an X-ray becomes a cone-beam (cone or pyramid-beam) shape or the like. The opening width of the collimator 103 is controlled by the system controller 124.

The transmission x-ray is irradiated from the X-ray tube device 101, passes through the collimator 103, is transmitted through an object, and then enters the X-ray detector 106.

In the X-ray detector 106, the X-ray detection element group is comprised of combinations of a scintillator and a photodiode, for example, approximately 1,000 pieces of the groups are arranged in the channel direction (circumferential direction), and approximately 1 to 320 pieces of the groups are arranged in the column direction (body-axis direction). The X-ray detector 106 is disposed oppositely to the X-ray tube device 101 across an object. The X-ray detector 106 detects an amount of X-rays irradiated from the X-ray tube device 101 and transmitted through the object and outputs the amount to the data collection device 107.

The data collection device 107 collects an X-ray amount to be detected by each X-ray detection element of the X-ray detector 106, converts the amount into digital data, and then sequentially outputs it to the image computing device 122 of the operation console 120 as transmission X-ray data.

The image computing device 122 acquires transmission X-ray data input from the data collection device 107 and generates projection data required for reconstruction after pre-processing such as logarithmic transformation and sensitivity correction. Because X-rays whose focal spots are alternately different for each view are irradiated from the X-ray tube device 101 when using the FFS method, the image computing device 122 generates FFS (+) projection data acquired using an X-ray irradiated from the first focal spot and FFS (−) projection data acquired using an X-ray irradiated from the second focal spot.

The image computing device 122 is provided with the virtual view generation unit 126 and the reconstruction computing unit 127.

The virtual view generation unit 126 generates a virtual view for focal shift projection data (FFS (+) projection data and FFS (−) projection data) scanned using the FFS method and inserts the view to generate up-sampled projection data. The virtual view is a view to be computed and inserted in a view position that is not scanned actually. Projection data of the virtual view can be calculated by interpolating or estimating based on actually scanned projection data (hereinafter, referred to as actual data). The detail of virtual view generation will be described later. Projection data generated (up-sampled) by the virtual view generation unit 126 is referred to as up-sampled projection data The reconstruction computing unit 127 reconstructs an image such as a tomographic image of an object using actually measured projection data (actual data of FFS (+) projection data and FFS (−) projection data) and up-sampled projection data generated by the virtual view generation unit 126.

In the present embodiment, the reconstruction computing unit 127 reconstructs an image using actual data (FFS (+) projection data and FFS (−) projection data) and up-sampled projection data in consideration of spatial resolution of the image. Specifically, actual data of FFS (+) projection data and FFS (−) projection data is used for reconstructing an image in the central region in the image plane, which improves spatial resolution in the central region. Also, an image is reconstructed using up-sampled projection data in the peripheral region of the image, which improves spatial resolution. That is, spatial resolution deteriorates in the peripheral region when FFS projection data is used in the entire region of the image, but up-sampled projection data is used for the peripheral region in the present embodiment, which is intended to improve the spatial resolution in the peripheral region. The up-sampled projection data can increase the number of views without reducing a rotational speed to insert a virtual view by computation. Therefore, it is particularly suitable for the case of generating an image of a moving site.

Either of an analytical method such as a filter correction reverse projection method or a successive approximation method may be used as the image reconstruction process.

Image data reconstructed by the image computing device 122 (the reconstruction computing unit 127) is input to the system controller 124, stored in the storage device 123, and displayed on the display device 125.

The system controller 124 is a computer provided with a CPU (Central Processing Unit), a ROM (Read Only Memory), a RAM (Random Access Memory), and the other. The storage device 123 is a data storage device such as a hard disk and stores a program, data, and the other for realizing functions of the X-ray CT apparatus 1 in advance.

Figure 2:
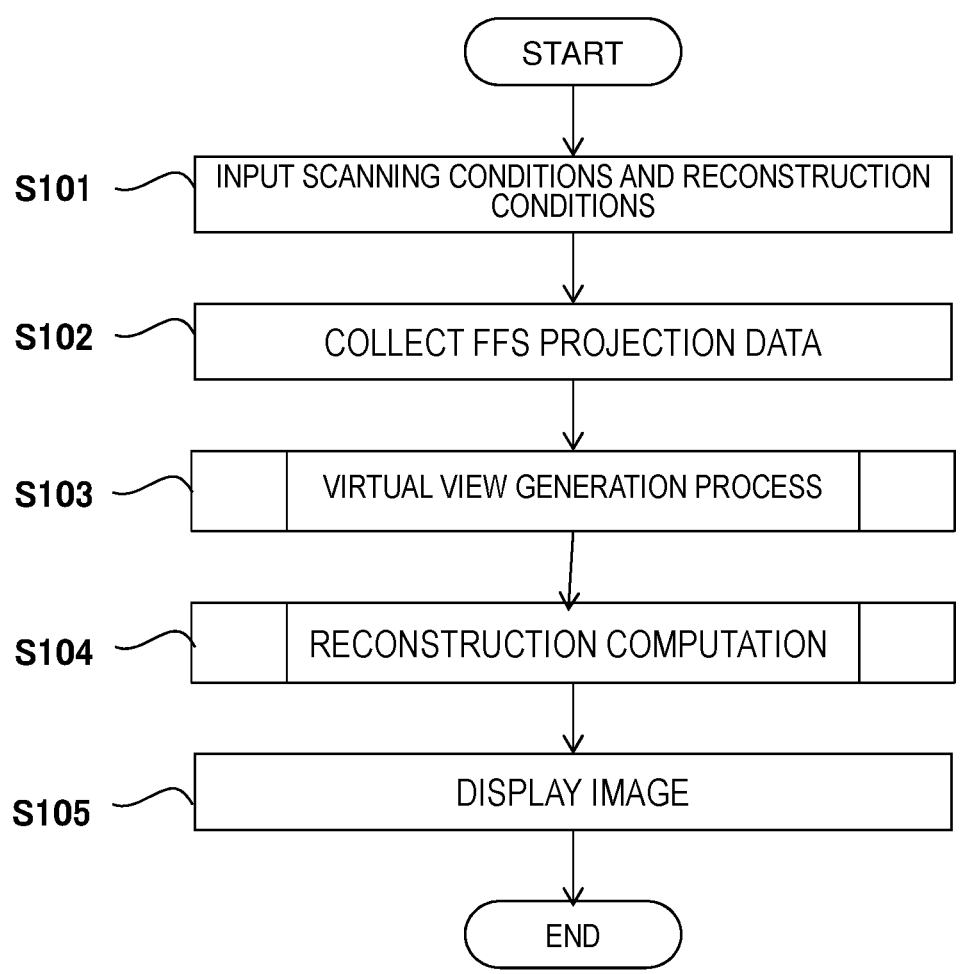
FIG. 2 is a flow chart explaining the entire process flow executed by the X-ray CT apparatus 1.

The system controller 124 performs a scanning process according to the processing procedure shown in FIG. 2. In the scanning process, the system controller 124 sends control signals according to the scanning conditions set by an operator to the focal shift X-ray controller 110 of the scan gantry unit 100, the bed controller 109, and the gantry controller 108 in order to control the above respective units. The details of each process will be described later.

The display device 125 is comprised of a liquid crystal panel, a display device such as a CRT monitor, and a logic circuit for executing a display process in association with the display device and is connected to the system controller 124. The display device 125 displays a reconstruction image output from the image computing device 122 as well as various information handled by the system controller 124.

The input device 121 is comprised of, for example, a pointing device such as a keyboard and a mouse, a numeric keypad, various switch buttons, and the like and outputs various commands and information to be input by an operator to the system controller 124. The operator interactively operates the X-ray CT apparatus 1 using the display device 125 and the input device 121. The input device 121 may be a touch panel-type input device integrally formed with the display screen of the display device 125.

Next, referring to FIGS. 2 to 15, the operations of the X-ray CT apparatus 1 will be described.

FIG. 2 is a flow chart explaining the entire scanning process flow executed by the X-ray CT apparatus 1 related to the present invention.

In the scanning process, the system controller 124 first receives inputs of scanning conditions and reconstruction conditions. The scanning conditions include X-ray conditions such as an X-ray tube voltage and an X-ray tube current, a scanning range, a gantry rotation speed, a bed speed, and the like. The reconstruction conditions include a reconstruction FOV, a reconstruction slice thickness, and the like.

After the scanning conditions and reconstruction conditions are input through the input device 121 or the like (Step S101), the system controller 124 sends control signals to the focal shift X-ray controller 110, the gantry controller 108, and the bed controller 109 based on the scanning conditions. The focal shift X-ray controller 110 controls the electric power to be input to the X-ray tube device 101 based on the control signal input from the system controller 124. Also, the focal shift X-ray controller 110 move an electronic beam irradiating to the rotating anode of the X-ray tube device 101 in a predetermined direction, by a predetermined distance, and at a predetermined timing in order to perform the FFS control that irradiates an X-ray by moving X-ray focal spots alternately. The gantry controller 108 controls the driving system of the rotary disk 102 according to the scanning conditions such as a rotational speed to rotate the rotary disk 102. The bed controller 109 adjusts the bed to a predetermined scanning start position based on a scanning range.

X-ray irradiation from the X-ray tube device 101 and transmission X-ray data measurement by the X-ray detector 106 are repeated along with the rotation of the rotary disk 102. The data collection device 107 acquires the transmission X-ray data measured by the X-ray detector 106 at various angles (views) around an object and sends the data to the image computing device 122. The image computing device 122 acquires the transmission X-ray data input from the data collection device 107 and performs pre-processing such as logarithmic transformation and sensitivity correction to generate projection data. Because scanning is performed by moving the X-ray focal spot to two positions using the FFS method in the present invention, the image computing device 122 generates FFS (+) projection data acquired by an X-ray irradiated from the first focal spot and FFS (−) projection data acquired by an X-ray irradiated from the second focal spot (Step S102).

The image computing device 122 (the virtual view generation unit 126) performs the virtual view generation process using the FFS (+) projection data and FFS (−) projection data (these are collectively referred to as FFS projection data) generated in the process of Step S102 (Step S103).

In the virtual view generation process, the virtual view generation unit 126 inserts a virtual view in an actual data (performs up-sampling) so as to have the predetermined number of views in order to generate up-sampled projection data. The number of views may be a value predetermined according to the device specifications or may be a value set by an operator. Also, the number of views may be a value determined by an image quality index (particularly spatial resolution) and the other parameters set by the operator. The specific method of the virtual view generation process will be described later (refer to FIGS. 3 to 12).

After generating up-sampled projection data in which a virtual view is inserted by the Step S103 process, the reconstruction computing unit 127 of the image computing device 122 next performs the image reconstruction process based on the reconstruction conditions input in Step S101 (Step S104). Any type of algorithm may be used as the image reconstruction algorithm to be used in the image reconstruction process. For example, a reverse projection process such as the Feldkamp method may be performed, and a successive approximation method or the like may be performed.

Figure 13:
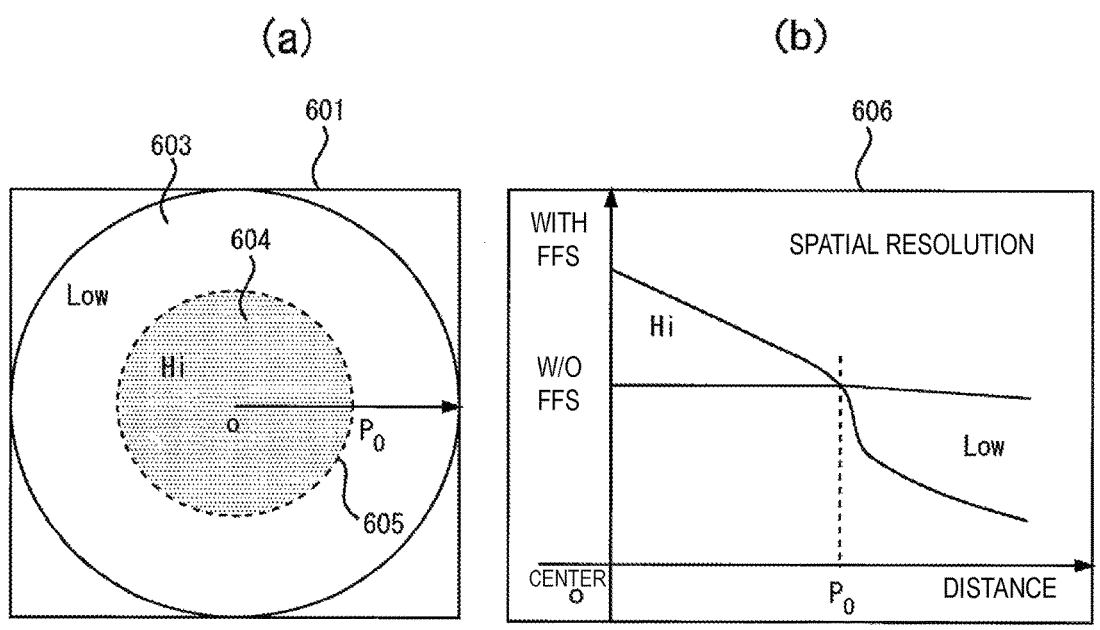
FIG. 13 is diagrams explaining a change of spatial resolution in the central region 604 and the peripheral region 603 of an image.

Conventionally, spatial resolution of an image reconstructed using FFS projection data can become higher in the central region of the image and become lower than when projection data without FFS is used as getting closer to the periphery, compared to when the FFS projection data is not used (refer to FIG. 13). Therefore, projection data up-sampled by a virtual view is used for a region of low spatial resolution (Low region: peripheral region) where FFS effects cannot be obtained, in the reconstruction computing process of Step S104 of the present invention. In a region where FFS effects can be obtained (Hi region: central region), an image is reconstructed using actual data of the FFS projection data (refer to FIGS. 13 to 15). The details of the reconstruction process will be described later.

After the image is reconstructed in Step S104, the system controller 124 displays the reconstructed image on the display device 125 (Step S105), and then a series of the scanning processes ends.

Next, each mode of the virtual view generation processes (A) to (D) of Step S103 will be described referring to FIGS. 3 to 10.

Figure 3:
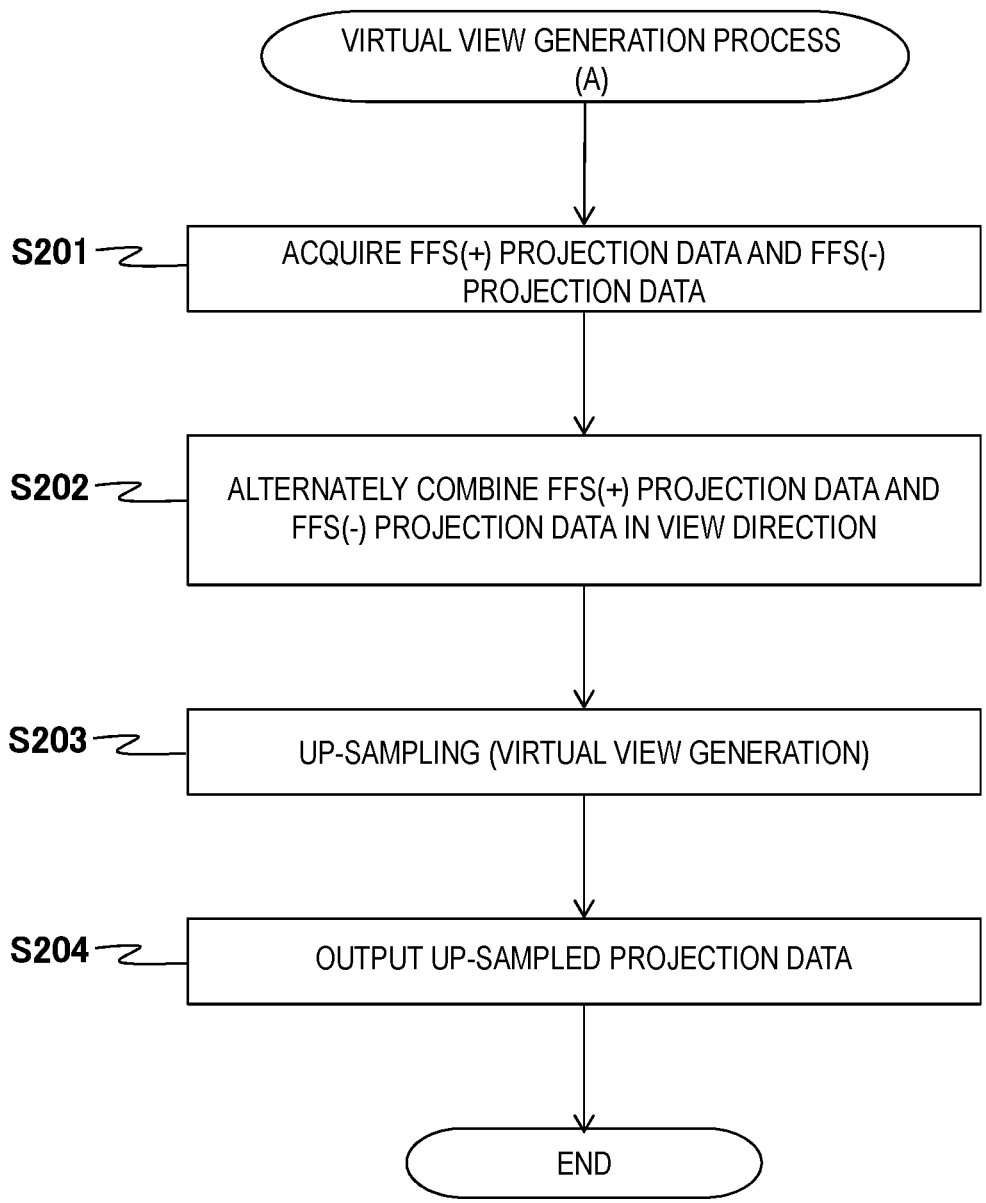
FIG. 3 is a flow chart explaining the flow of the virtual view generation process (A).
Figure 4:
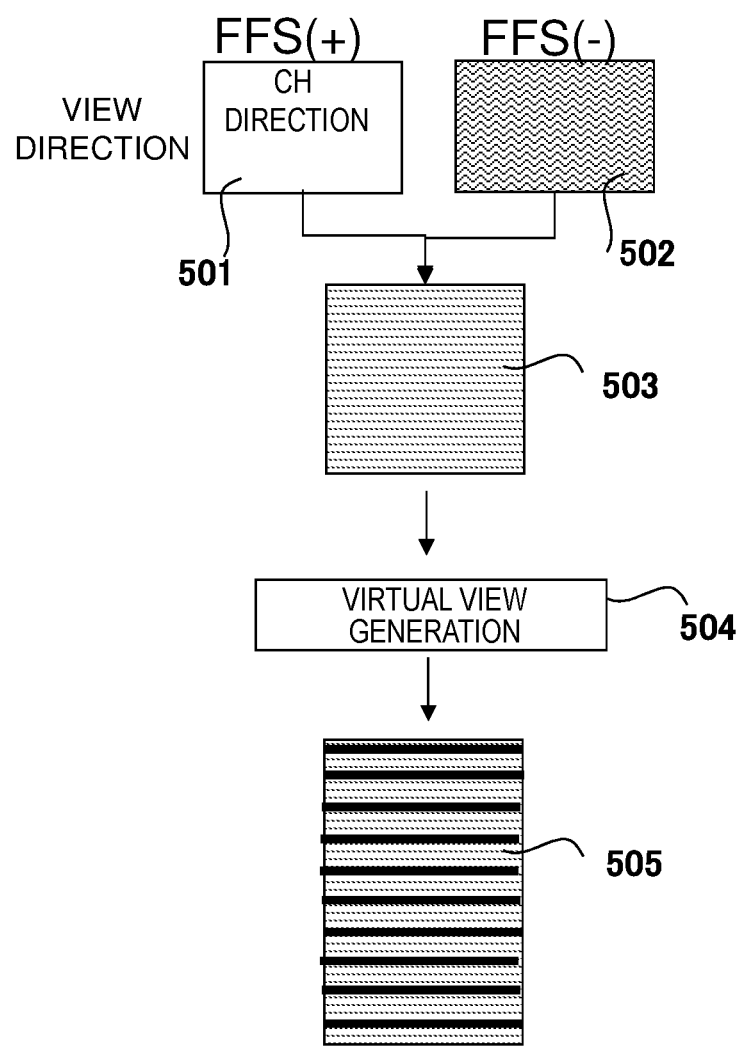
FIG. 4 is a schematic diagram showing the procedure of the virtual view generation process (A).

First, the virtual view generation process (A) will be described referring to FIGS. 3 and 4.

The image computing device 122 acquires the FFS (+) projection data 501 and the FFS (−) projection data 502 by moving a focus of the X-ray tube device 101 (Step S201), and then acquires the FFS projection data 503 by alternately combining the FFS (+) projection data 501 and the FFS (−) projection data 502 in the view direction (Step S202). Furthermore, the virtual view generation 504 is executed for the FFS projection data 503 (Step S203) to acquire the up-sampled projection data 505. The virtual view generation unit 126 outputs the up-sampled projection data 505 to the reconstruction computing unit 127 (Step S204).

Figure 5:
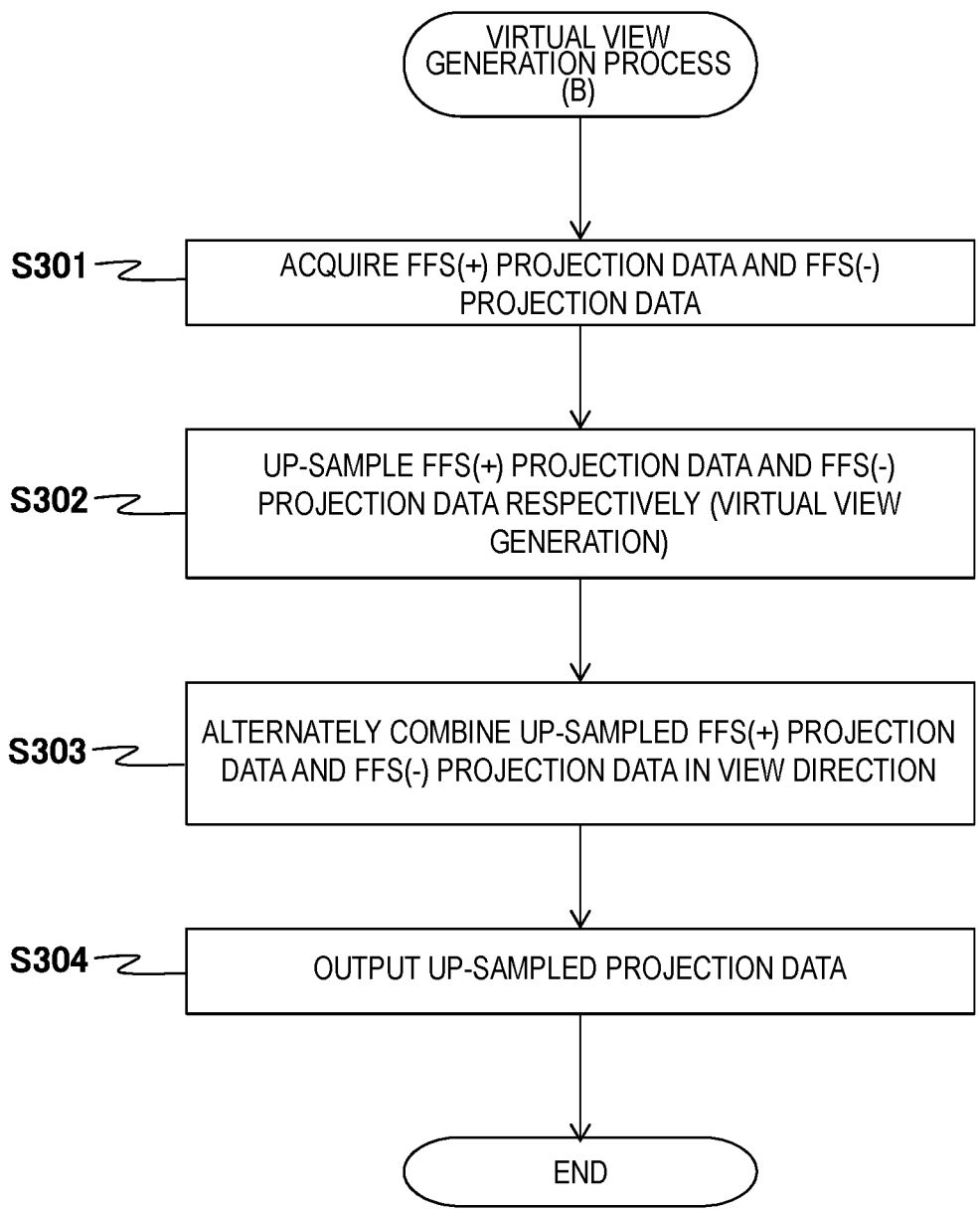
FIG. 5 is a flow chart explaining the flow of the virtual view generation process (B).
Figure 6:
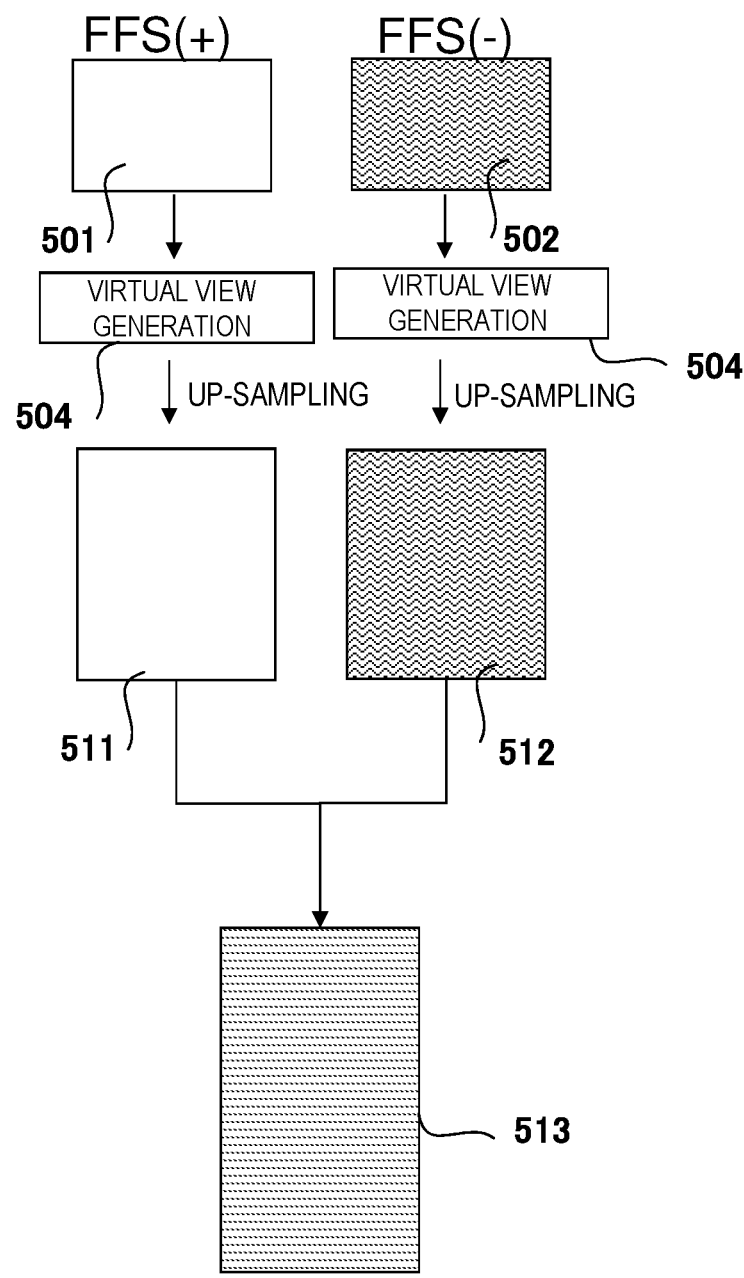
FIG. 6 is a schematic diagram showing the procedure of the virtual view generation process (B).

The virtual view generation process (B) will be described referring to FIGS. 5 and 6.

The image computing device 122 acquires the FFS (+) projection data 501 and the FFS (−) projection data 502 by moving a focus of the X-ray tube device 101 (Step S301) and then executes the virtual view generation 504 for the FFS (+) projection data 501 and the FFS (−) projection data 502 respectively (Step S302). Then, the FFS projection data 513 is acquired by alternately combining the up-sampled FFS (+) projection data 511 and FFS (−) projection data 512 in the view direction (Step S303). The virtual view generation unit 126 outputs the up-sampled projection data 513 to the reconstruction computing unit 127 (Step S304).

Figure 7:
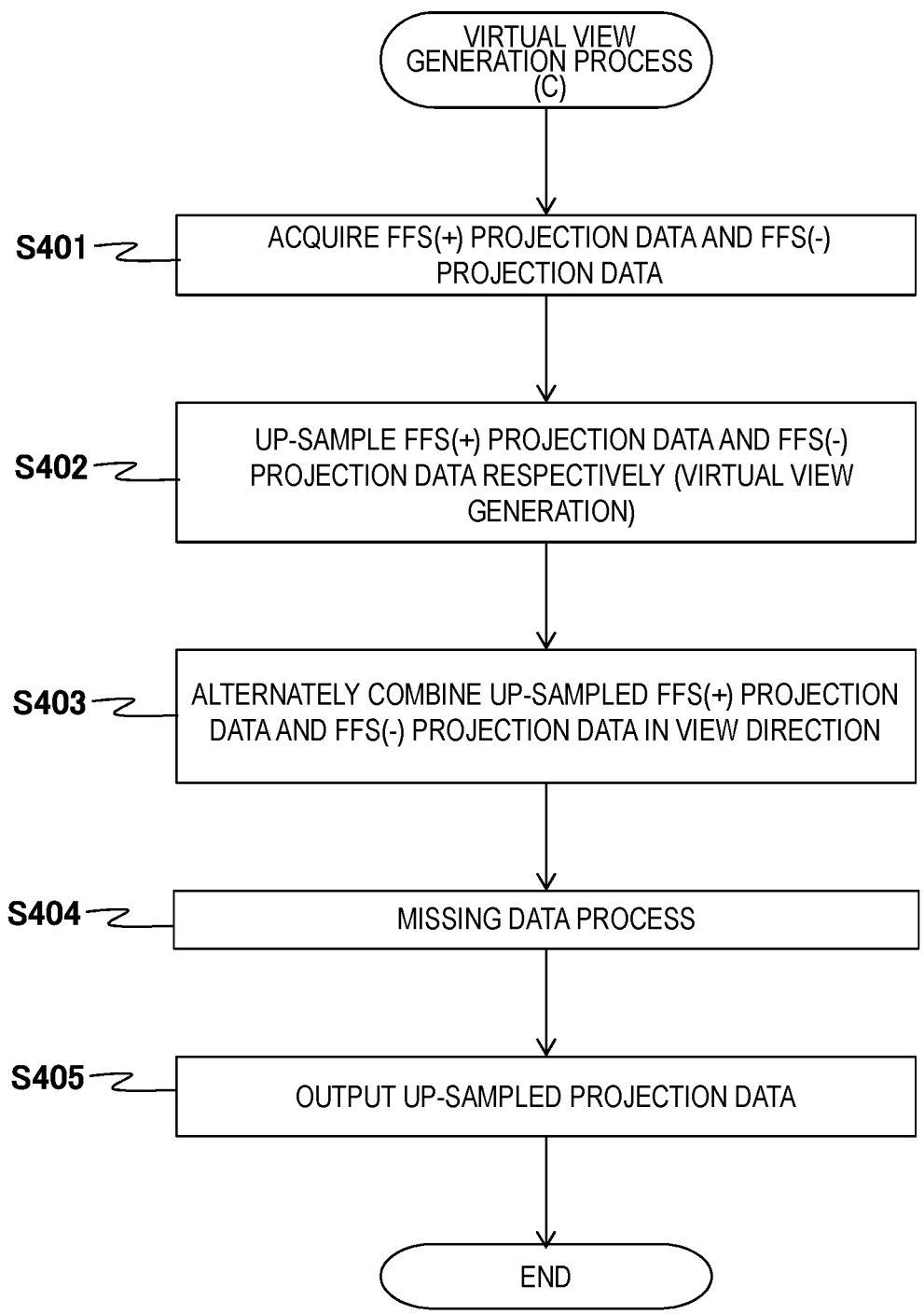
FIG. 7 is a flow chart explaining the flow of the virtual view generation process (C).
Figure 8:
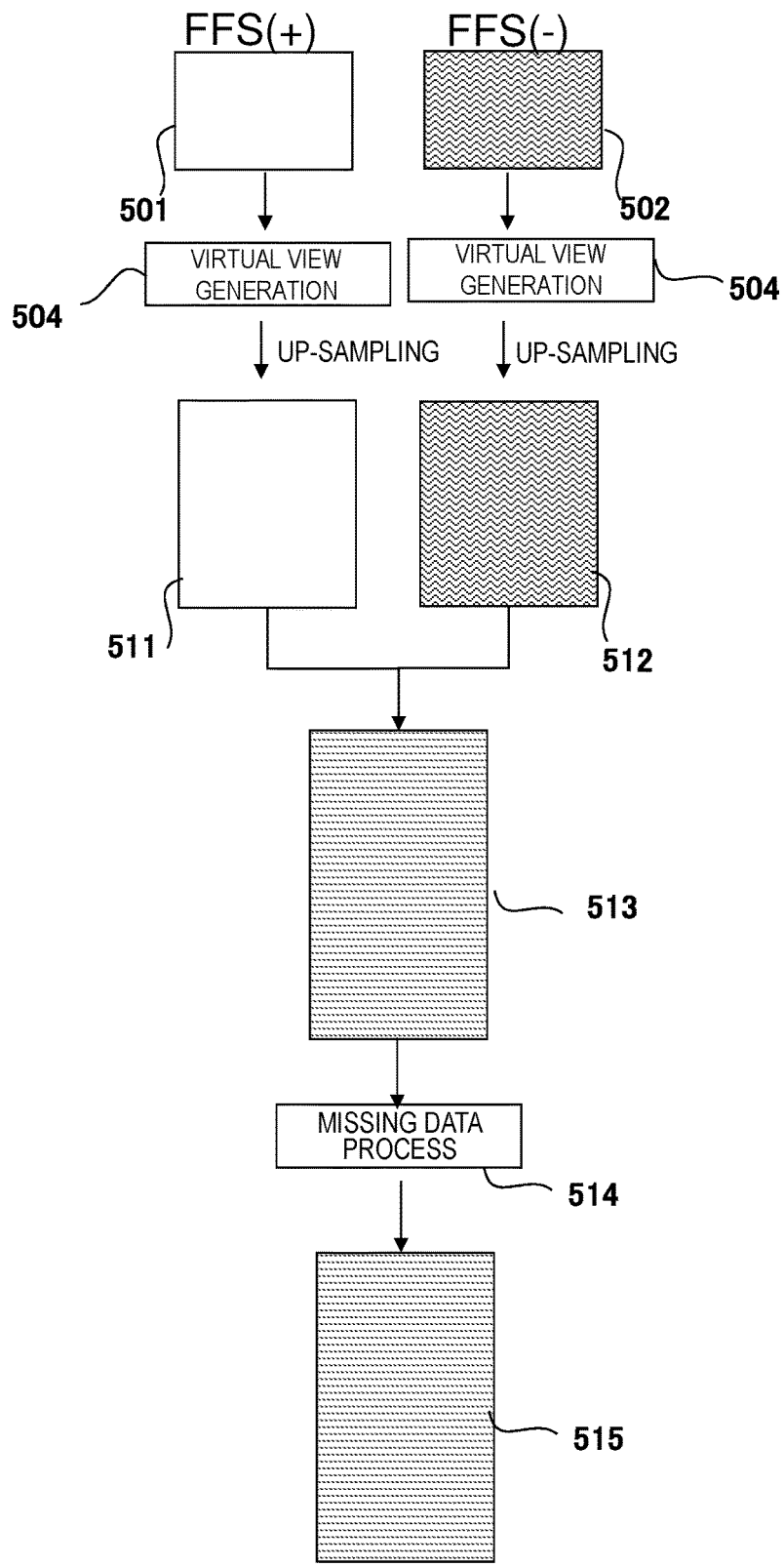
FIG. 8 is a schematic diagram showing the procedure of the virtual view generation process (C).

The virtual view generation process (C) will be described referring to FIGS. 7 and 8.

The image computing device 122 acquires the FFS (+) projection data 501 and the FFS (−) projection data 502 by moving a focus of the X-ray tube device 101 (Step S401) and then executes the virtual view generation 504 for the FFS (+) projection data 501 and the FFS (−) projection data 502 respectively (Step S402). Then, the up-sampled FFS projection data 513 is acquired by alternately combining the up-sampled FFS (+) projection data 511 and FFS (−) projection data 512 in the view direction (Step S403).

The virtual view generation unit 126 further performs the missing data process 514 for the up-sampled FFS projection data 513 (Step S404).

The missing data process is a process for alternately combining FFS (+) projection data and FFS (−) projection data in the view direction to fill missing data caused in the FFS projection data 513 acquired by interpolating and estimating the missing data using projection data or that in the vicinity adjacent in the view direction and the channel direction. The FFS (+) projection data and FFS (−) projection data acquired by moving a focal spot in the channel direction have different X-ray paths respectively. Therefore, the data to be acquired is twice the number of channels. When measuring projection data for each view during scanning by alternately moving focal spots, FFS (+) projection data is acquired in odd views, FFS (−) projection data is acquired in even views, and these data is combined alternately, which causes alternate missing data for each view in the FFS projection data 513.

In the process of Step S404, the missing data process 514 is performed to fill such missing data.

After acquiring the up-sampled projection data 515 for which the missing data process 514 was performed in Step S404, the virtual view generation unit 126 outputs the up-sampled projection data 515 to the reconstruction computing unit 127 (Step S405).

Figure 9:
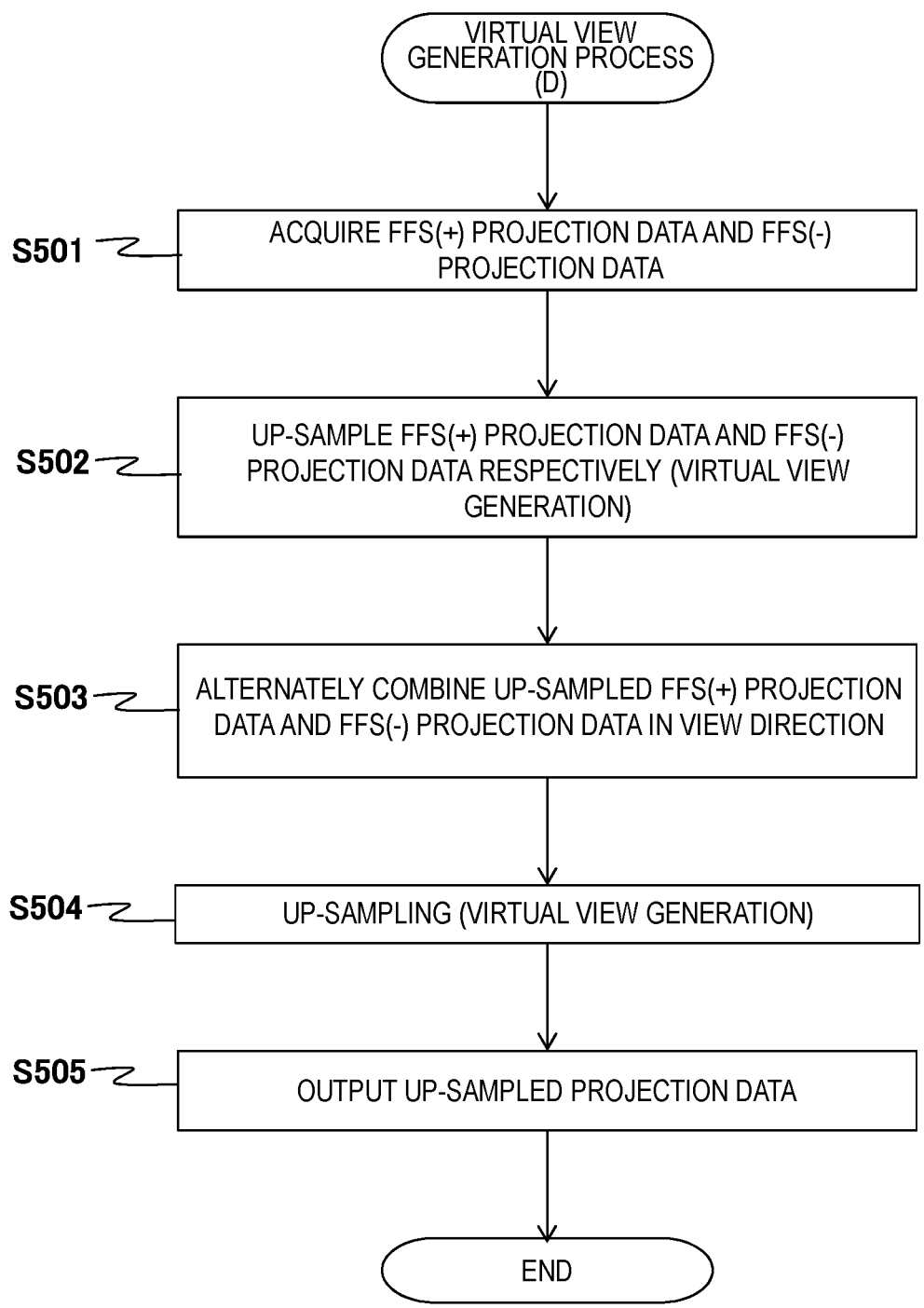
FIG. 9 is a flow chart explaining the flow of the virtual view generation process (D).
Figure 10:
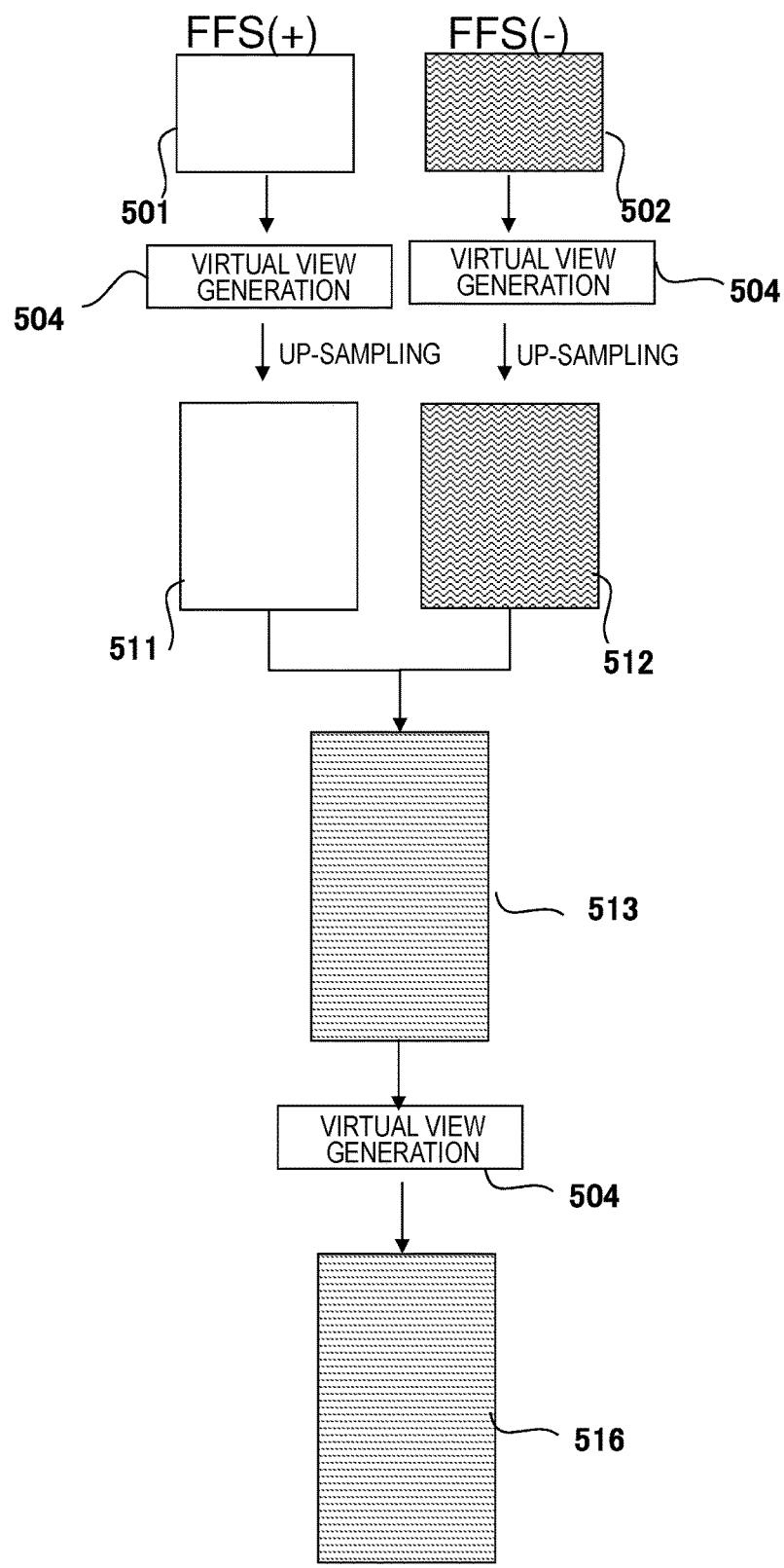
FIG. 10 is a schematic diagram showing the procedure of the virtual view generation process (D).

The virtual view generation process (D) will be described referring to FIGS. 9 and 10.

The image computing device 122 acquires the FFS (+) projection data 501 and the FFS (−) projection data 502 by moving a focus of the X-ray tube device 101 (Step S501) and then executes the virtual view generation 504 for the FFS (+) projection data 501 and the FFS (−) projection data 502 respectively (Step S502). Then, the up-sampled FFS projection data 513 is acquired by alternately combining the up-sampled FFS (+) projection data 511 and FFS (−) projection data 512 in the view direction (Step S503).

The virtual view generation unit 126 further executes the virtual view generation 504 for the up-sampled FFS projection data 513 (Step S504). The process of Step S504 acquires the up-sampled FFS projection data 516. The virtual view generation unit 126 outputs the up-sampled projection data 516 to the reconstruction computing unit 127 (Step S505).

Here, the virtual view calculating method (up-sampling method) will be described referring to FIG. 11. Each up-sampling method shown in FIG. 11 can be applied to any of the virtual view generation processes in Step S203 of FIG. 3, Step S302 of FIG. 5, Step S402 of FIG. 7, and Steps S502 and S504 of FIG. 9.

The virtual view generation unit 126 (the image computing device 122) calculates projection data of the virtual view by interpolation or estimation for views (virtual views) to be inserted using projection data near the view or channel direction, data of the counter Ray (counter data), projection data near the view or channel direction of the counter data, or the like.

(Up-Sampling Method for Generating a Virtual View Using Counter Data)

In projection data acquired in one-rotation (2π) scanning, a virtual view can be generated using data of the counter Ray (hereinafter, the data of the counter Ray is referred to as the counter data). Referring to FIGS. 11(*a*) and 11(*b*), an example of generating a virtual view for the projection data acquired in one-rotation scanning using the counter data to double the number of the views will be described.

Figure 11:
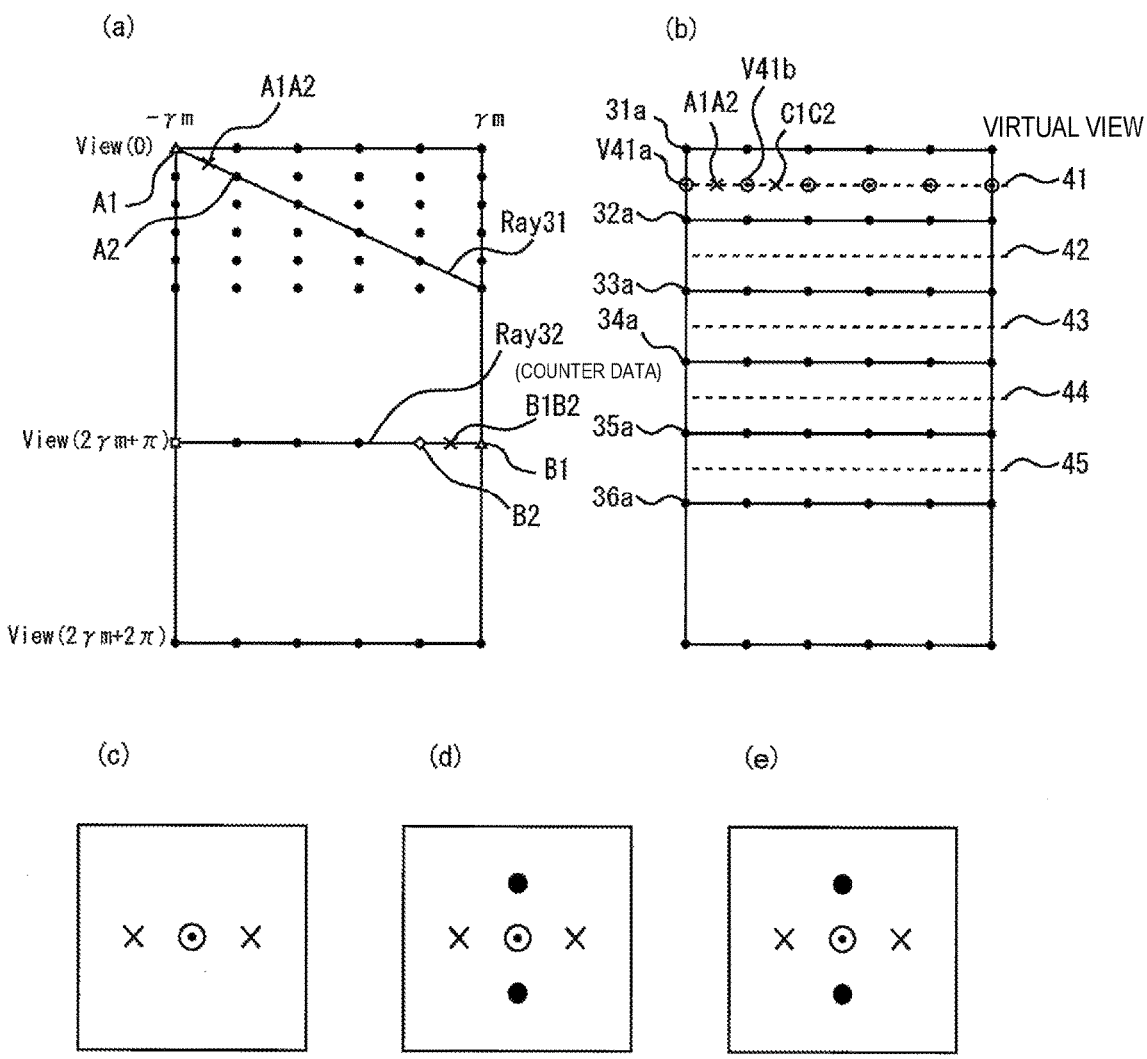
FIGS. 11(a) and 11(b) are diagrams explaining the up-sampling method using counter data.
FIGS. 11(c), 11(d), and 11(e) are diagrams showing interpolation between two points, interpolation between four points, and interpolation by the TV method respectively.

In the projection data of one rotation shown in FIG. 11(*a*), Ray31 and Ray32 are counter to each other. That is, they are on the same X-ray irradiation path. The counter data at the points A1 and A2 of Ray31 are respectively the points B1 and B2 of Ray32. The points B1 and B2 are the data of the adjacent channel on the actual view (2γm+π) as shown in FIG. 11(*a*). The relationship between the points A1 and B1 on the projection data can be expressed in the following formula (1) using the function R (γ, θ) that uses parameters in which γ represents the channel direction and θ represents the view direction.

[Formula 1]

$$R_{A1}(-\gamma_m, 0) = R_{B1}(\gamma_m, 2\gamma_m + \pi) \quad (1)$$

Also, the relationship between the channel and the view at the points A1 and B1 can be expressed in the following formulas (2) and (3).

[Formula 2]

$$\begin{cases} \gamma_{A1} = -\gamma_{B1} \\ \theta_{A1} = \theta_{B1} - 2\gamma_{B1} + \pi \end{cases} \quad (2)\\(3)$$

Hence, the point A1 A2 in the virtual view 41 between the points A1 and A2 can be calculated in the following formulas (4) and (5) as the point B1B2 calculated from the points B1 and B2 on the actual view (2γm+π).

[Formula 3]

$$\begin{cases} \gamma_{A1A2} = \dfrac{\gamma_{A1} + \gamma_{A2}}{2} = -\left(\dfrac{\gamma_{B1} + \gamma_{B2}}{2}\right) & (4) \\ \theta_{A1A2} = \dfrac{\theta_{A1} + \theta_{A2}}{2} = \left(\dfrac{\theta_{B1} + \theta_{B2}}{2}\right) - 2\left(\dfrac{\gamma_{B1} + \gamma_{B2}}{2}\right) + \pi & (5) \end{cases}$$

Using the similar procedure, a point adjacent by one pixel (the point C1C2 of FIG. 11(*b*)) in the virtual view 41 is calculated from the counter data, which can generate channel data (the point V41*b*) by linear interpolation shown with a double circle of FIG. 11(*b*). This operation is repeated to calculate each channel data of the virtual view 41. Channel data at each point can be similarly calculated using the counter data for the other virtual views 41, 42, and the subsequent views.

In the virtual view generation method (up-sampling method) using counter data, each channel data of virtual views is calculated based on the counter data (actual data) having biological information (measurement data transmitted through an object) closest to channel data to be estimated (the points shown with double circles). The counter data having the closest biological information means a Ray that has the closest transmission path among the measured Rays and enters from the opposite direction. The above counter data is characterized by obtaining a Ray selectively and calculating a virtual Ray γ estimated from the selected Ray to generate a virtual view. By using this method, only the number of views can be up-sampled while the number of channels is not changed. Although channel data of virtual views is calculated using an average value of two points of counter data in case of double sampling, the channel data may be calculated by linear interpolation between two points or non-linear interpolation in case of N-times sampling. Also, this method enables up-sampling in the channel direction to be performed simultaneously.

Additionally, the virtual view generation method is not limited to the up-sampling method using the counter data as described above. The method to be used may be the two-point interpolation that simply interpolates the adjacent views each other as shown in FIG. 11(*c*), the four-point interpolation that interpolates using the adjacent views and the channel data as shown in FIG. 11(*d*), or the interpolation by the TV (Total Variation) method as shown in FIG. 11(*e*).

Also, the number of views of up-sampled projection data may be set to the arbitrary number of views including a decimal value such as 1.5 times of actual data. For example, when the number of views is increased partially in the view direction, the number is in multiples of a decimal value. The object 2 has a cross section with a shape close to an ellipse as shown in FIG. 12(*a*). Therefore, as shown in FIG. 12(*b*), the up-sampled projection data 518 in multiples of a decimal value can also be generated by increasing the number of partial views such as making the number of views dense in a view equivalent to the long diameter of an ellipse.

Figure 14:
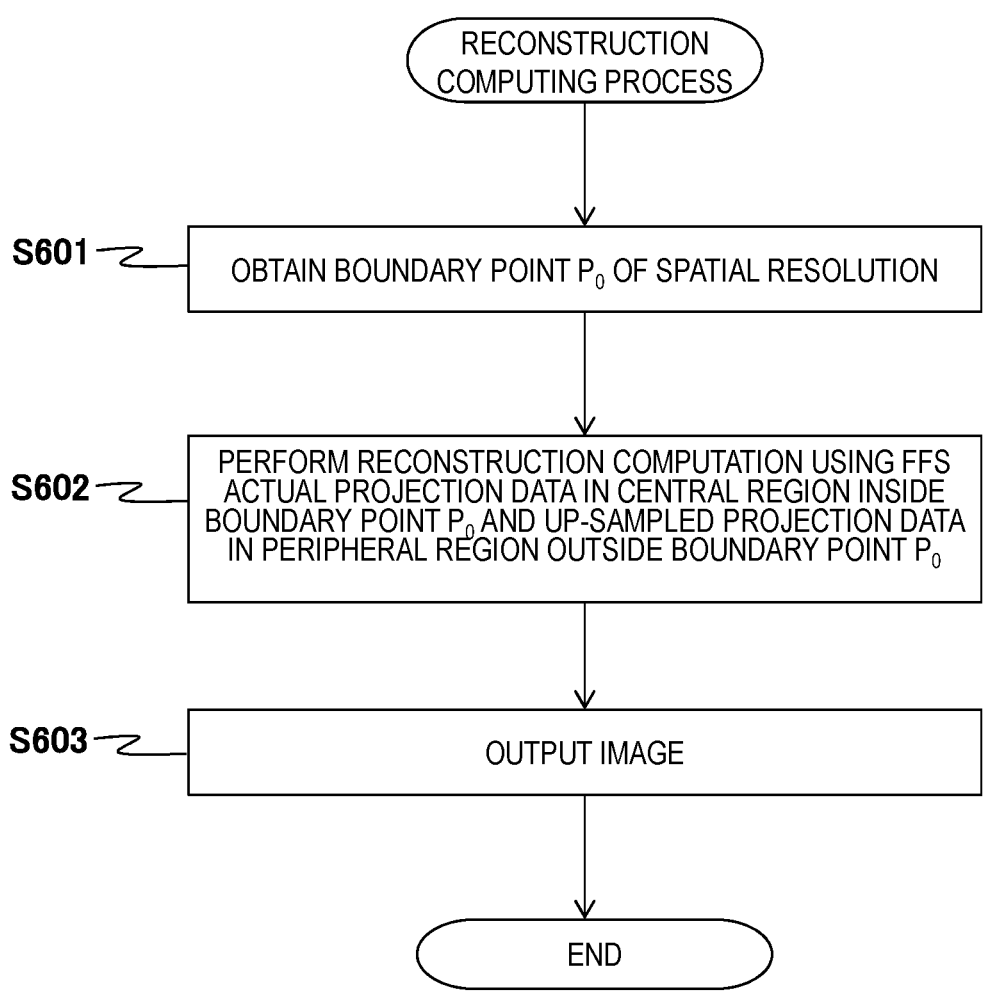
FIG. 14 is a flow chart explaining the flow of the reconstruction computing process.
Figure 15:
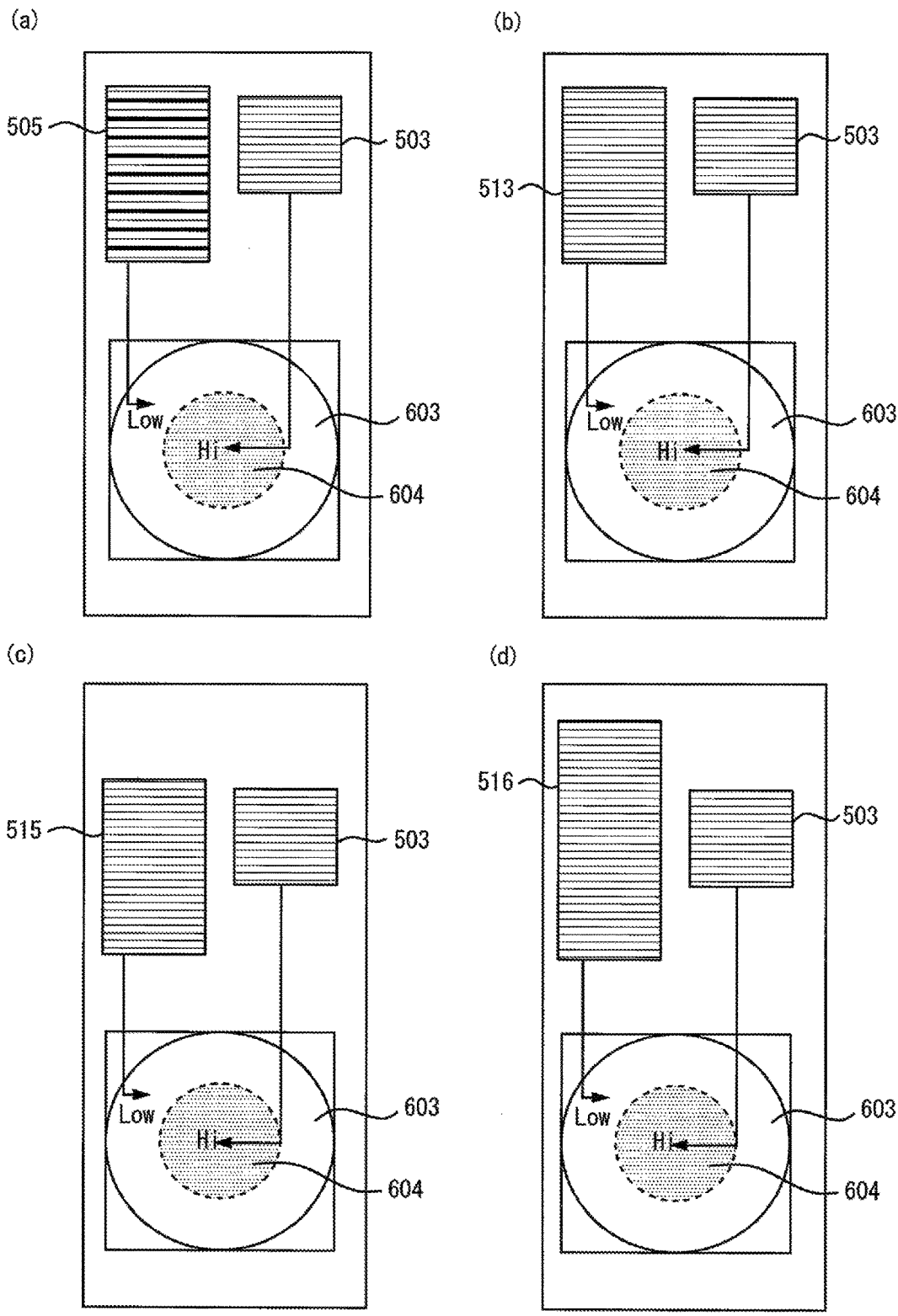
FIG. 15 is a diagram showing modes of the projection data to be used for the reconstruction computing process of FIG. 14.

Next, the reconstruction computing process in Step S104 of FIG. 2 will be described referring to FIGS. 13 to 15.

As described above, spatial resolution of an image to be reconstructed using FFS projection data can become higher in the central region of the image and become lower than when projection data without FFS is used as getting closer to the periphery, compared to when the FFS projection data is not used (refer to FIG. 13).

FIG. 13(b) is the graph 606 showing the relationship between a distance from the center O and spatial resolution in the tomographic image 601 shown in FIG. 13(a). Compared to when using projection data without FFS, spatial resolution (indicated by an index) is higher in a region inside the boundary 605 (hereinafter, referred to as the central region 604) in a distance from the image center O to the point $P_0$ when FFS projection data is used. On the other hand, spatial resolution (indicated by an index) is lower compared to when using projection data without FFS in a region (hereinafter, referred to as the peripheral region 603) outside the boundary point $P_0$ (the boundary 605 shown in FIG. 13(a)).

Therefore, spatial resolution of the peripheral region 603 is improved by performing image reconstruction for data of the central region 604 already having sufficient spatial resolution using FFS projection data (actual data) that is not up-sampled and performing image reconstruction in the peripheral region 603 using projection data that is up-sampled by virtual view generation.

Hence, spatial resolution can be improved in the central region 604 while prevented from being affected by data generation, and the number of views is improved in the peripheral region 603 without reducing a rotational speed by generating a virtual view, which can improve the spatial resolution.

The procedure for the reconstruction computing process will be described referring to the flow chart of FIG. 14.

First, the reconstruction computing unit 127 obtains the boundary point $P_0$ of spatial resolution (Step S601). The boundary point $P_0$ is a distance from the scanning center of a position where spatial resolution acquired by FFS projection data and that acquired by projection data without FFS are reversed. This boundary point $P_0$ is calculated by experimental data in advance and stored in the storage device 123 or the like.

As an evaluation index of spatial resolution, MTF (Modulation Transfer Function) is used. For example, the above boundary point $P_0$ may be calculated for each different spatial resolution evaluation index such as MTF50%, 10%, and 2% in order to allow an operator to select it. Since required image quality is different according to the examination and the diagnostic purpose, it desirable that required spatial resolution can be selected according to the balance with the other image quality (such as noise).

Alternatively, a boundary point to be the gravity center may be calculated from the boundary point $P_0$ obtained by a plurality of spatial resolution indexes such as MTF50%, 10%, and 2%.

The reconstruction computing unit 127 uses actual data of FFS projection data in the central region 604 on the central side from the boundary point $P_0$ and up-sampled projection data that up-sampled FFS projection data in the peripheral region 603 on the outside of the boundary point $P_0$ in order to perform reconstruction computation (Step S602).

As the up-sampled projection data to be used in the peripheral region 603, up-sampled projection data generated by any method of the above virtual view generation processes (A) to (D) may be used. That is, the up-sampled projection data that may be used is the up-sampled projection data 505 generated in the virtual view generation process (A) shown in FIGS. 3 and 4 as shown in FIG. 15(a), the up-sampled projection data 513 generated in the virtual view generation process (B) shown in FIGS. 5 and 6 as shown in FIG. 15(b), the up-sampled projection data 515 generated in the virtual view generation process (C) shown in FIGS. 7 and 8 as shown in FIG. 15(c), or the up-sampled projection data 516 generated in the virtual view generation process (D) shown in FIGS. 9 and 10 as shown in FIG. 15(d).

Also, the virtual view generation method of any of the up-sampled projection data 505, 513, 515, and 516 may adopt the up-sampling method using counter data, interpolation with two points adjacent in the view direction, interpolation with four points adjacent in the view and channel directions, interpolation using the TV method etc., or the like as described above.

In the reconstruction computation, image reconstruction such as a reverse projection process may be performed after synthesizing actual data of FFS projection data with up-sampled projection data on projection data, or an image may be generated by synthesizing a portion corresponding to the central region 604 of an image reconstructed using the actual data of FFS projection data and a portion corresponding to the peripheral region 603 of an image reconstructed using the up-sampled projection data.

The reconstruction computing unit 127 outputs an image generated by the process in Step S602 (Step S603). The output destination is, for example, the storage device 123, the display device 125, and the like.

As described above, the X-ray CT apparatus 1 of the first embodiment up-samples focal shift projection data (FFS projection data) acquired by shifting an X-ray focal spot in the X-ray tube device 101 in the view direction. Then, in the image reconstruction computing process, an image is reconstructed using actual data of FFS projection data in the central region 604 closer to the scanning center than a predetermined boundary point $P_0$ and up-sampled projection data that up-sampled FFS projection data in the peripheral region 603 farther from the scanning center than the boundary point $P_0$.

Because data up-sampled by a virtual view is used for the periphery of an effective field of view, there is no need to perform scanning by reducing a rotational speed to increase the number of views. Therefore, spatial resolution of the periphery is improved regardless of the rotational speed limit and the like due to hardware limitation, which can improve spatial resolution of the entire effective field of view. It is suitable to scan a moving site.

Second Embodiment

Next, the second embodiment of the present invention will be described referring to FIGS. 16 to 18.

The X-ray CT apparatus 1 of the second embodiment performs the joint process so that spatial resolution continues smoothly at the boundary point $P_0$ in the reconstruction computing process.

Figure 16:
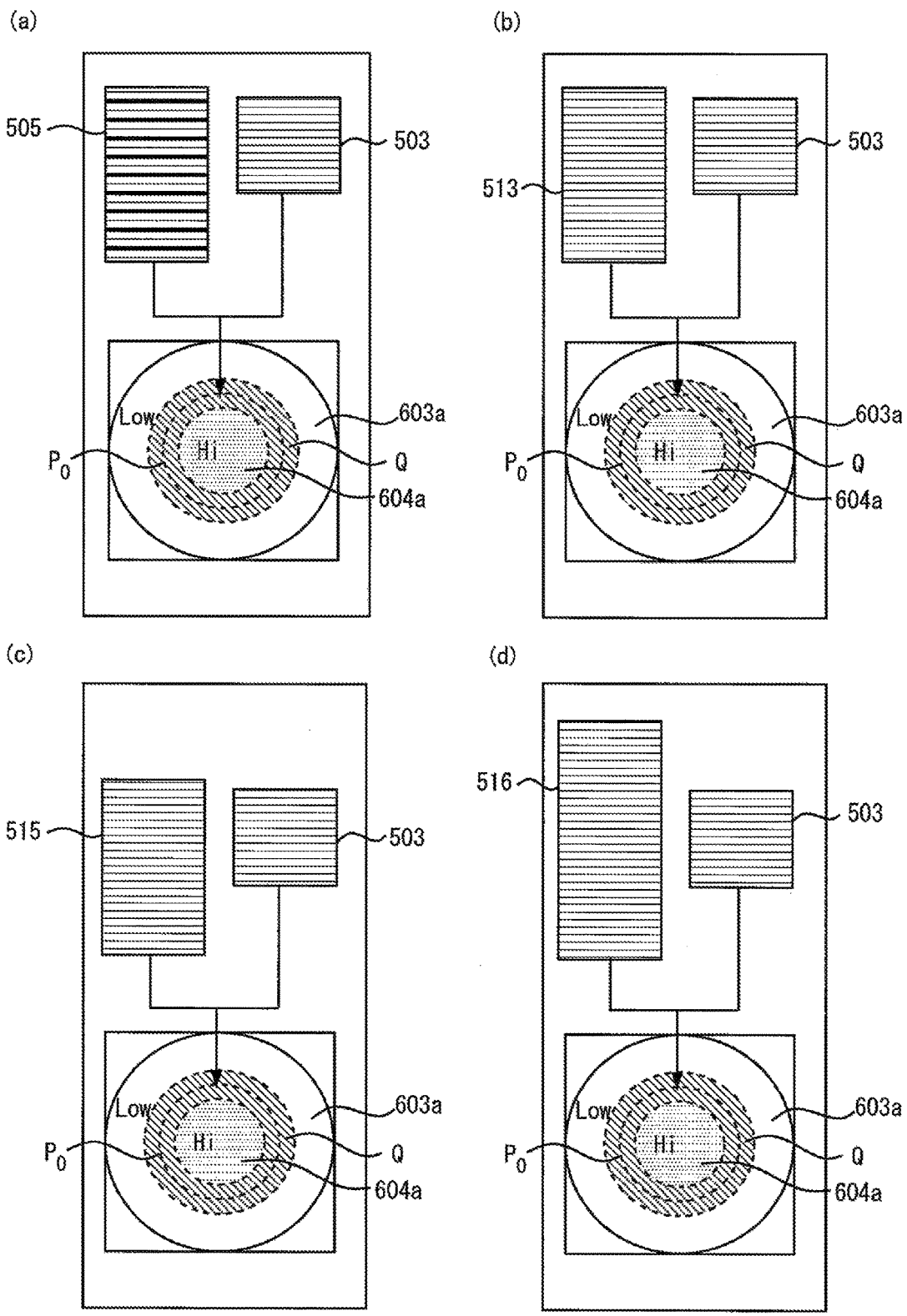
FIG. 16 is a diagram explaining the reconstruction computing process of the second embodiment.

In the joint process, as shown in FIG. 16, both an image reconstructed by FFS projection data and an image reconstructed by up-sampled projection data are synthesized at a predetermined rate in a region of a predetermined range including the boundary point $P_0$ (hereinafter, referred to as the boundary region Q). In the central region 604a closer to the center than the boundary region Q, an image reconstructed by actual data of FFS projection data is used 100% similarly to the first embodiment. In the peripheral region 603a outside the boundary region Q, an image reconstructed by up-sampled projection data is used 100% similarly to the first embodiment.

That is, according to the distance from the center, an image reconstructed by FFS projection data and an image reconstructed by up-sampled projection data are synthesized while changing the weights each other.

Figure 17:
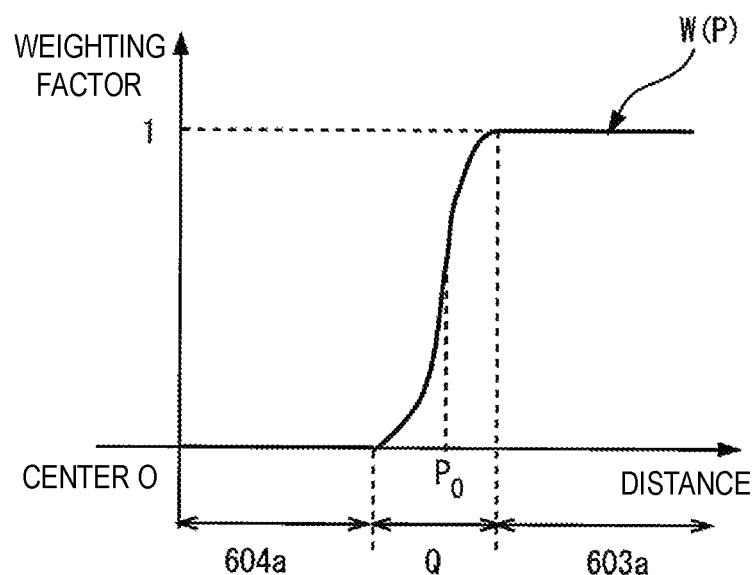
FIG. 17 shows an example of a weighting factor to be applied in the reconstruction computing process of the second embodiment.

FIG. 17 is a graph showing a weighting factor to be applied to a reconstruction image by up-sampled projection data. As shown in FIG. 17, the weighting factor W(P) changes according to the distance P from the center O. The weighting factor W(P) is "0" in the central region 604a, a curve rising smoothly in the boundary region Q, and "1" in the peripheral region 603a. Although the weighting factor to be applied to a reconstruction image by FFS projection data also changes according to the distance P from the center O, the weighting factor W(P) is "1" in the central region 604a, a curve falling smoothly in the boundary region Q, and "0" in the peripheral region 603a on the contrary to that shown in FIG. 17.

The range of the boundary region Q is set arbitrarily, and it may be changed according to the desired spatial resolution of a desired region.

Also, although the weighting factor is shown in a smooth curve that depends on the distance P from the image center in the example of FIG. 17, it is not limited to this and may be shown in a straight line or bend line.

Also in the second embodiment, as shown in FIGS. 16(a) to 16(d), up-sampled projection data generated by any of the above virtual view generation processes (A) to (D) may be used for the peripheral region 603a and the boundary region Q. That is, the up-sampled projection data that may be used is the up-sampled projection data 505 generated by the virtual view generation process (A) shown in FIGS. 3 and 4 as shown in FIG. 16(a), the up-sampled projection data 513 generated by the virtual view generation process (B) shown in FIGS. 5 and 6 as shown in FIG. 16(b), the up-sampled projection data 515 generated by the virtual view generation process (C) shown in FIGS. 7 and 8 as shown in FIG. 16(c), or the up-sampled projection data 516 generated by the virtual view generation process (D) shown in FIGS. 9 and 10 as shown in FIG. 16(d).

Also, the virtual view of any of the up-sampled projection data 505, 513, 515, and 516 may be calculated using a method of interpolation between two points adjacent in the view direction (FIG. 11(c)), interpolation between four points adjacent in the view direction and the channel direction (FIG. 11(d)), or interpolation or estimation by the TV method etc. (FIG. 11(e)) or using counter data (FIGS. 11(a) and 11(b)) as described above.

The number of views of up-sampled projection data is not limited to the double of actual data and may be more than the double. By partially increasing the number of views in the view direction, the arbitrary number of views including a decimal value such as 1.5 times may be set.

Figure 18:
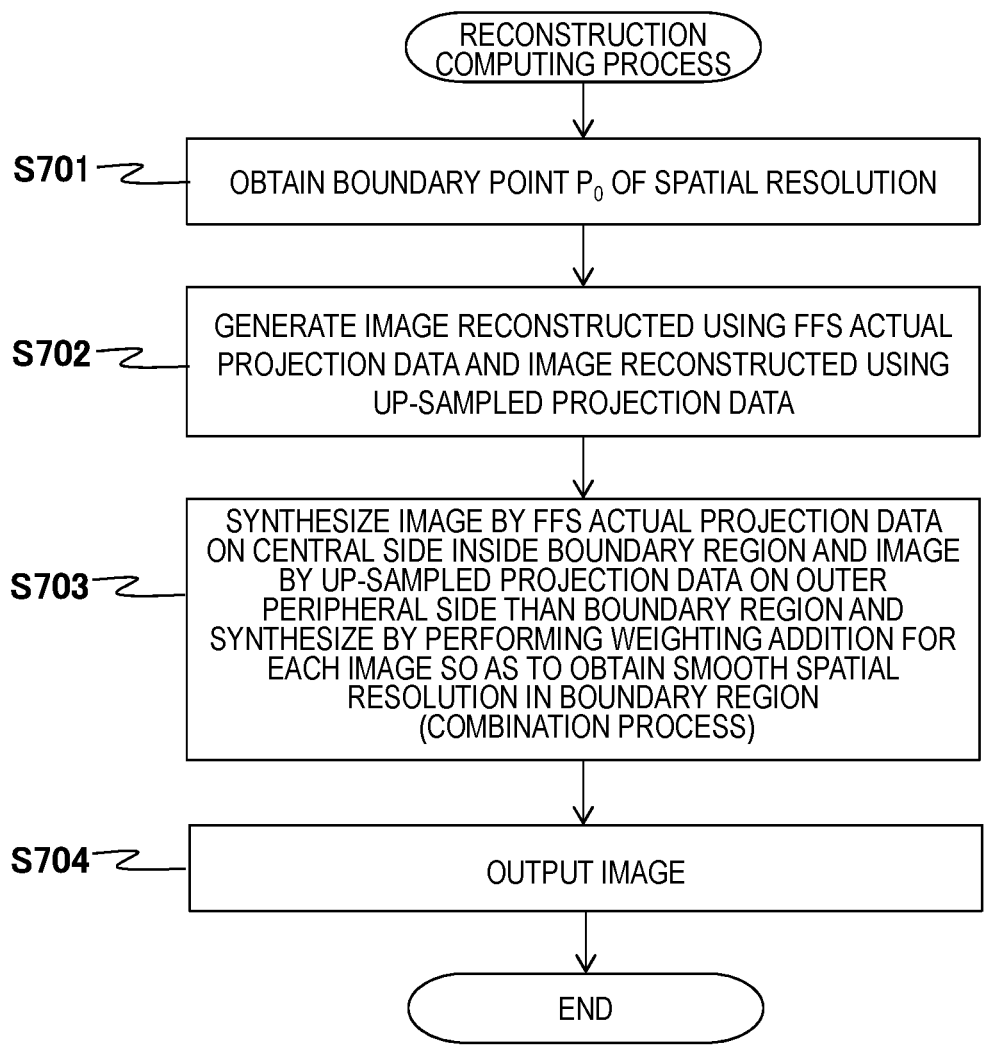
FIG. 18 is a flow chart explaining the flow of the reconstruction computing process of the second embodiment.

Referring to FIG. 18, the flow of the reconstruction computing process of the second embodiment will be described.

First, the reconstruction computing unit 127 obtains the boundary point $P_0$ of spatial resolution (Step S701). The method of obtaining the boundary point $P_0$ is similar to the first embodiment (Step S601 of FIG. 14).

Next, the reconstruction computing unit 127 generates an image reconstructed using actual data of FFS projection data and an image reconstructed using up-sampled projection data for which the FFS projection data was up-sampled (Step S702).

Next, the reconstruction computing unit 127 uses the image reconstructed by actual data of FFS projection data in the central region 604a closer to the center than the boundary region Q including the boundary point $P_0$ to generate a synthesized image using the image reconstructed by up-sampled projection data in the peripheral region 603a outside the boundary region Q. In the boundary region Q, weighted addition is performed for each image reconstructed in Step S702 so as to be continuous spatial resolution (Step S703). As described above, in the weighted addition, for example, an image generated by the up-sampled projection data is multiplied by a weighting factor of the shape shown in FIG. 17, an image generated by the actual data of FFS projection data is multiplied by a weighting factor of the shape opposite to the graph shown in FIG. 17, and these images are added.

The reconstruction computing unit 127 outputs an image generated by the process of Step S703 (Step S704). The output destination is, for example, the storage device 123, the display device 125, and the like.

As described above, the X-ray CT apparatus 1 of the second embodiment uses actual data of FFS projection data in the central region 604a close to the center in the image reconstruction computing process to synthesize each image generated using up-sampled projection data in the peripheral region 603a closer to the peripheral side than the boundary point $P_0$. Additionally, in the predetermined boundary region Q, weighted addition is performed for each of the above images so that spatial resolution continues smoothly.

Hence, in addition to the effectiveness of the first embodiment, an image in which spatial resolution continues smoothly in the boundary region Q can be acquired.

Additionally, although weighted addition is performed to synthesize reconstructed images in the above reconstruction computing process, synthesized projection data may be reconstructed after synthesizing up-sampled projection data and actual data of FFS projection data on the projection data. In this case, the projection data to be used is that generated by performing weighted addition for up-sampled projection data and actual data of FFS projection data in a part corresponding to the boundary region Q.

Third Embodiment

Next, referring to the FIGS. 19 and 20, the third embodiment of the present invention will be described.

In the X-ray CT apparatus 1 of the third embodiment, it may be configured so that an image using actual data of FFS projection data and an image using up-sampled projection data are synthesized by changing weight over the entire image.

Figure 19:
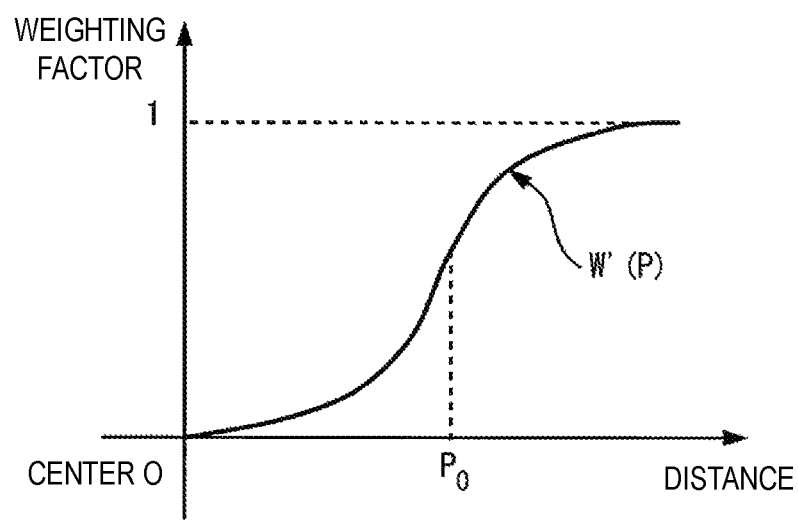
FIG. 19 shows an example of a weighting factor to be applied in the reconstruction computing process of the third embodiment.

FIG. 19 is a graph showing the weighting factor W'(P) to be applied to a reconstruction image by up-sampled projection data in the third embodiment. This graph rises smoothly from "0" in a region close to the center and becomes "1" at the end of the peripheral region. That is, the graph has a shape in which a weighting factor changes according to the distance from the center O even in a region other than the boundary region Q. Thus, the graph shape of the weighting factor may be arbitrary, the weighting factor is changed so as to acquire desired spatial resolution in a desired region even in a region other than the boundary region Q.

Additionally, on the contrary to FIG. 19, a weighting factor to be applied to a reconstruction image by FFS actual projection data smoothly falls from "1" in the region close to the center and becomes "0" at the end of the peripheral region.

Although the weighting factor W'(P) is shown in a smooth curve that depends on the distance P from the image center in the example of FIG. 19, the weighting factor W'(P) is not limited to this and may be shown also in a straight line.

Figure 20:
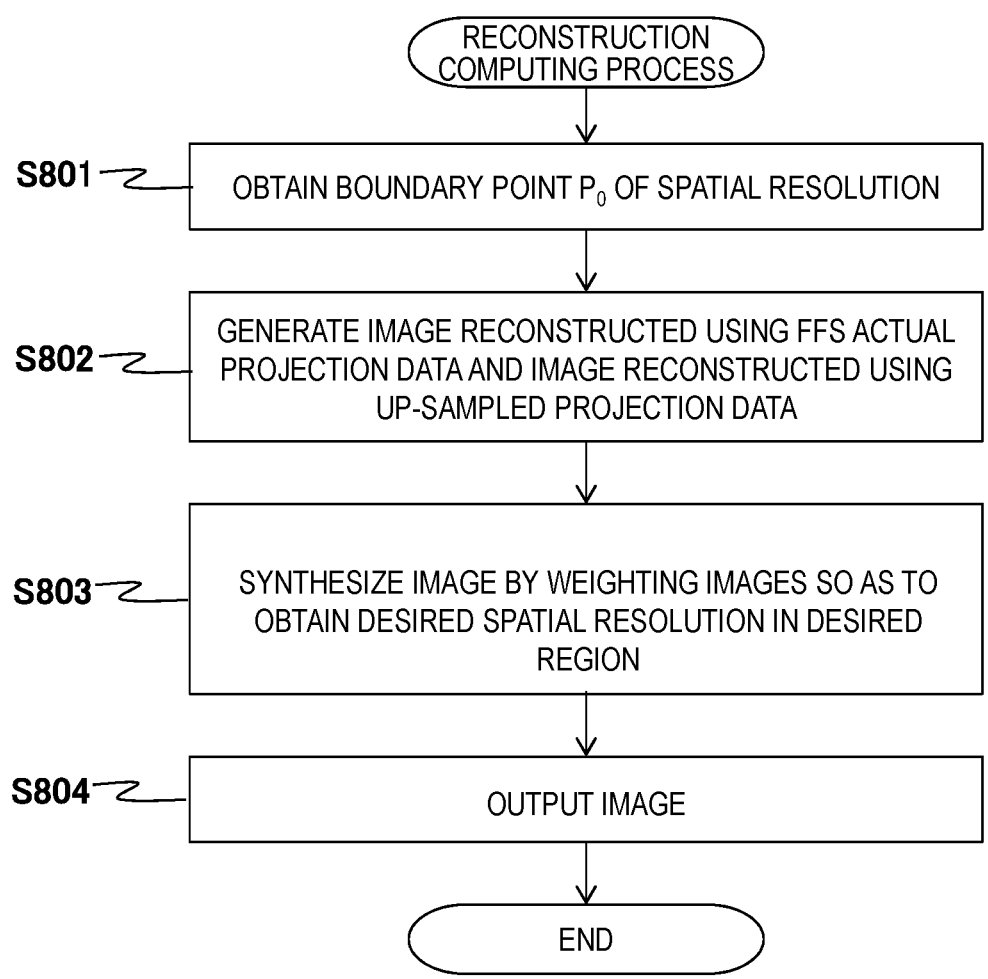
FIG. 20 is a flow chart explaining the flow of the reconstruction computing process of the third embodiment.

Referring to FIG. 20, the flow of the reconstruction computing process in the third embodiment will be described.

First, the reconstruction computing unit 127 obtains the boundary point $P_0$ of spatial resolution (Step S801). The boundary point $P_0$ is obtained similarly to the first embodiment (Step S601 of FIG. 14).

Next, the reconstruction computing unit 127 generates an image reconstructed using actual data of FFS projection data and an image reconstructed using up-sampled projection data for which the FFS projection data was up-sampled (Step S802).

The up-sampled projection data that may be used is that generated using any of the virtual view generation processes (A) to (D).

Next, the reconstruction computing unit 127 applies a weighting factor of a desired shape to each image and adds it (Step S803). The weight is used for synthesizing an image reconstructed using actual data of FFS projection data and an image reconstructed using up-sampled projection data for which the FFS projection data was up-sampled at an appropriate rate so as to acquire desired spatial resolution in a desired region.

Then, the reconstruction computing unit 127 outputs an image generated by the process of Step S803 (Step S804). The output destination is, for example, the storage device 123, the display device 125, and the like.

As described above, the X-ray CT apparatus 1 of the third embodiment synthesizes an image reconstructed by actual data of FFS projection data and an image reconstructed by up-sampled projection data using a weighting factor that changes according to the distance from the scanning center in the image reconstruction computing process.

Hence, in addition to the effectiveness of the first embodiment, an image that becomes desired spatial resolution in a desired region in the image can be acquired. Also, a highly reliable image can be acquired in a desired region by increasing the weight of the actual data.

Fourth Embodiment

Next, referring to FIGS. 21 and 22, the fourth embodiment of the present invention will be described.

In the fourth embodiment, as shown in FIG. 21, the actual data 503 of FFS projection data is applied to the region of interest (ROI) 7 set by an operator and the central region 604. Also, the up-sampled projection data 505 is applied to the peripheral region 603. When the ROI 7 is in the peripheral region 603, the actual data 503 of the FFS projection data is used for the range within the ROI 7.

Figure 22:
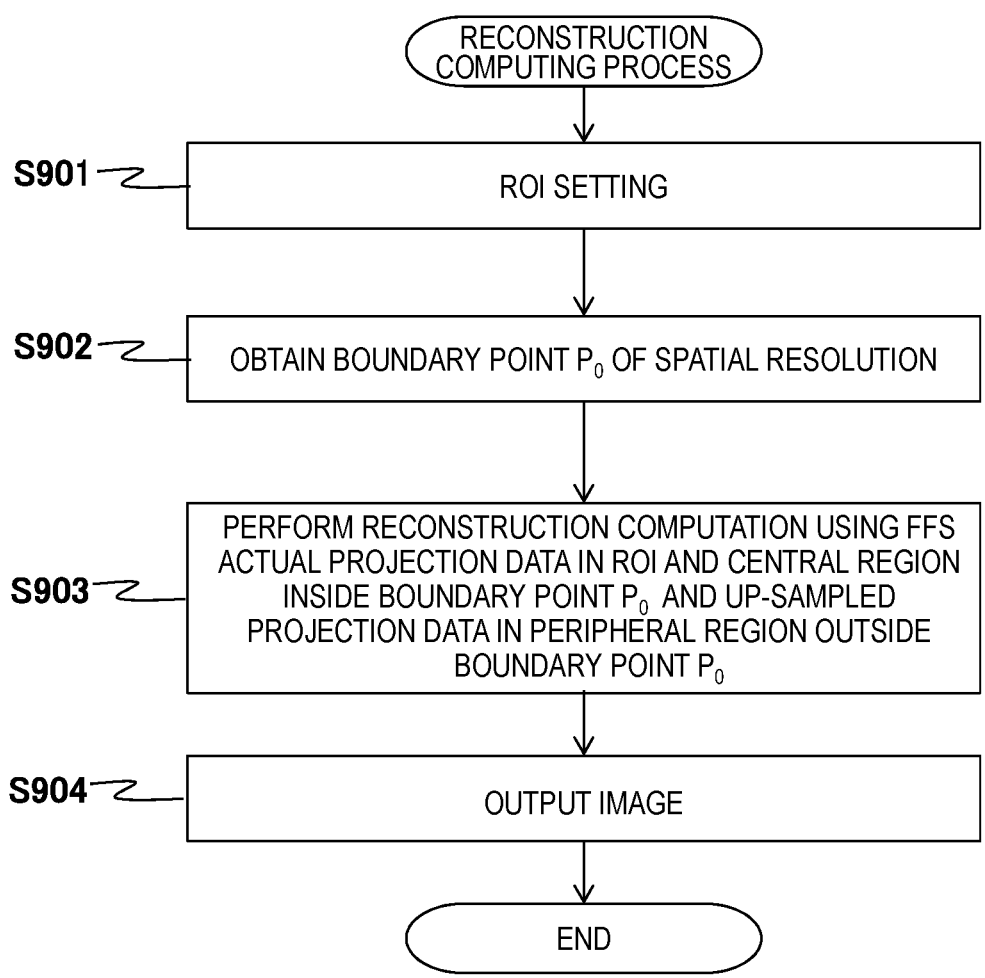
FIG. 22 is a flow chart explaining the flow of the reconstruction computing process of the fourth embodiment.

Referring to FIG. 22, the flow of the reconstruction computing process of the fourth embodiment will be described.

First, the system controller 124 and the region of interest (ROI) 7 are set (Step S901). The setting of the ROI 7 is performed by an operator through the input device 121. Next, the reconstruction computing unit 127 obtains the boundary point $P_0$ of spatial resolution (Step S902). The boundary point $P_0$ is obtained similarly to the first embodiment (Step S601 of FIG. 14).

Next, the reconstruction computing unit 127 reconstructs an image using actual data of FFS projection data in the ROI 7 set in Step S901 and the central region 604 or up-sampled projection data by a virtual view in the peripheral region 603 excluding the ROI 7 (Step S903).

The up-sampled projection data that may be used is that generated using any of the virtual view generation processes (A) to (D).

The reconstruction computing unit 127 outputs an image generated by the process of Step S903 (Step S904). The output destination is, for example, the storage device 123, the display device 125, and the like.

As described above, the X-ray CT apparatus 1 of the fourth embodiment enhances the image reliability by reconstructing an image using actual data of FFS projection data in the ROI 7 and the central region 604. Also, spatial resolution is improved using up-sampled projection data in the peripheral region 603 excluding the ROI 7. Hence, it is possible to acquire an image whose reliability is high in a ROI to be diagnosed and the image center and whose spatial resolution of the periphery is improved.

Also in the fourth embodiment, the joint process shown in the second embodiment may be performed in the boundary region Q, and weighted addition may be performed for an image by FFS projection data and an image by up-sampled projection data using a weighting factor of a desired shape shown in the third embodiment.

Fifth Embodiment

Next, referring to FIGS. 23 to 25, the fifth embodiment of the present invention will be described.

Figure 23:
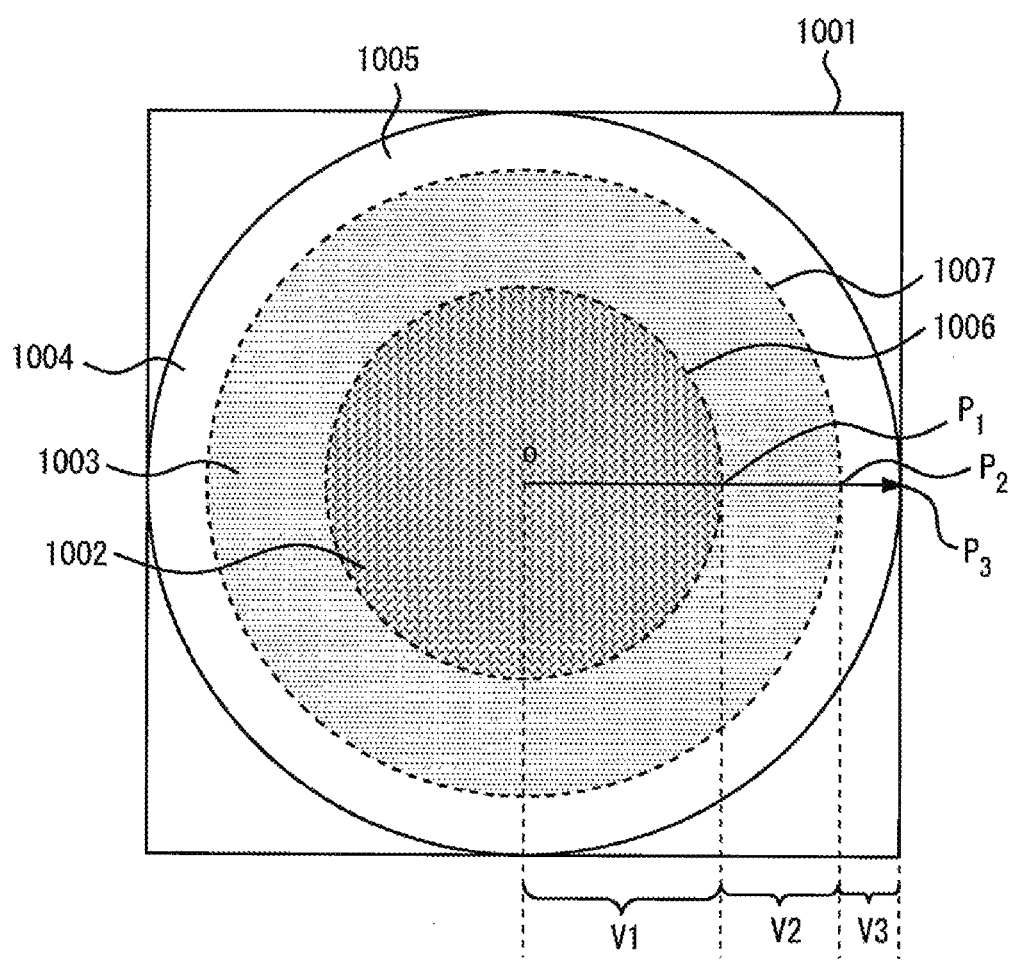
FIG. 23 shows an example of synthesizing an image reconstructed using projection data up-sampled by the number of views different depending on the distance from the image center in the reconstruction computing process of the fifth embodiment.

As shown in FIG. 23, in the fifth embodiment, the reconstruction computing unit 127 synthesizes images reconstructed using FFS projection data of the number of respectively different views (the number of up-sampling) for the region 1002 from the center O to the distance P1, the region 1003 from the distance P1 to the distance P2, and the region 1004 from the distance P2 to the distance P3 within the reconstruction image 1001. For example, the number of views V1 is set for actual data of FFS projection data in the region 1002, FFS projection data up-sampled to the number of views V2 is used in the region 1003, and FFS projection data up-sampled to the number of views V3 is used in the region 1004.

When each image before synthesis of the regions 1002, 1003, and 1004 is set as $\xi(V1)$, $\xi(V2)$, and $\xi(V3)$, the image $\xi(V)$ after synthesis can be expressed in the following formula (6).

[Formula 4]

$$\xi(V)=\xi(V1)+\xi(V2)+\xi(V3) \qquad (6)$$

The up-sampled projection data may be that generated using any of the virtual view generation processes (A) to (D) described in the first embodiment.

Figure 24:
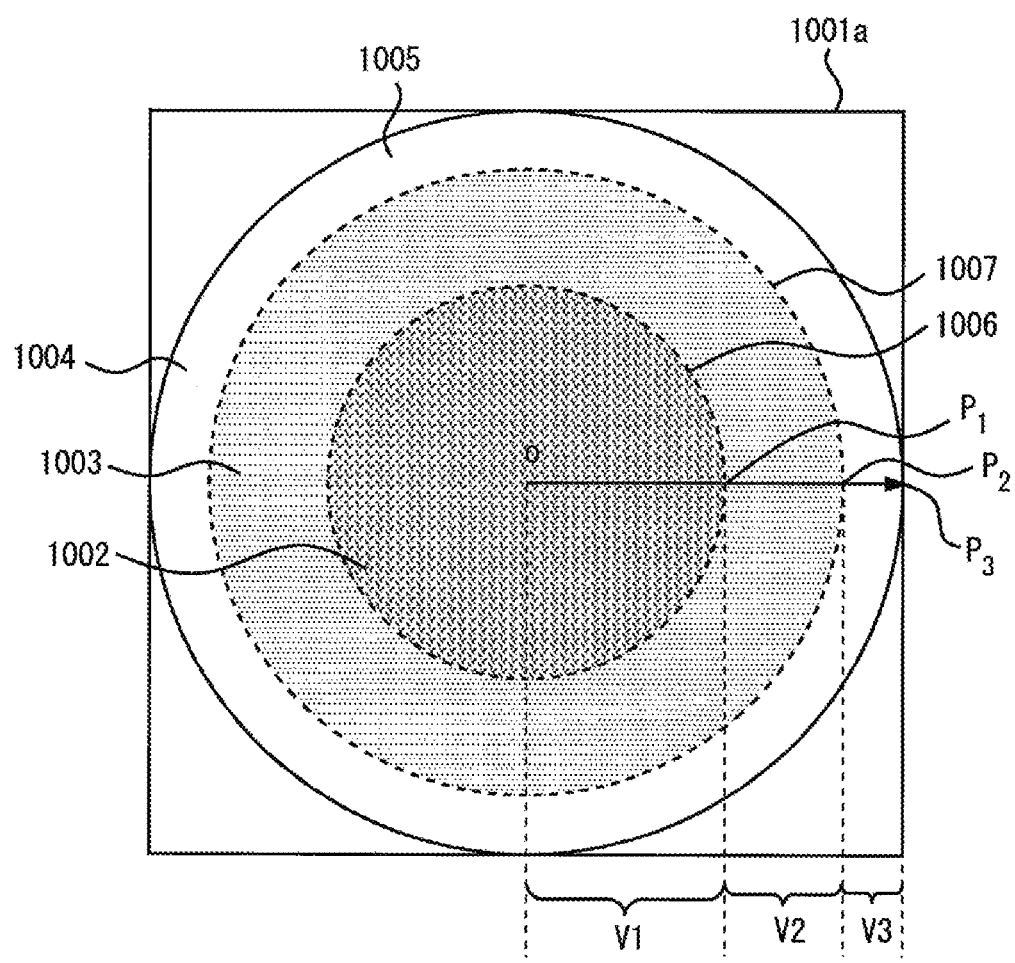
FIG. 24 shows an example of synthesizing an image by weighting so as to smooth the region near the boundary in the example of FIG. 23.

Also, as shown in the image 1001a of FIG. 24, the joint process may be performed so as to acquire continuous spatial resolution in the boundary portions between the region 1002 and the region 1003 and between the region 1003 and the region 1004. The joint process is similar to the second embodiment. That is, the images $\xi(V1)$, $\xi(V2)$, and $\xi(V3)$ are reconstructed by projection data of each view number using the weighting factors $W(V1)$, $W(V2)$, and $W(V3)$ that change the spatial resolution continuously and smoothly before synthesizing the images in the boundary portions 1006 and 1007.

The synthesized image $\xi(V)$ can be expressed in the following formula (7).

[Formula 5]

$$\xi(V)=W(V1)\xi(V1)+W(V2)\xi(V2)+W(V3)\xi(V3) \qquad (7)$$

Figure 25:
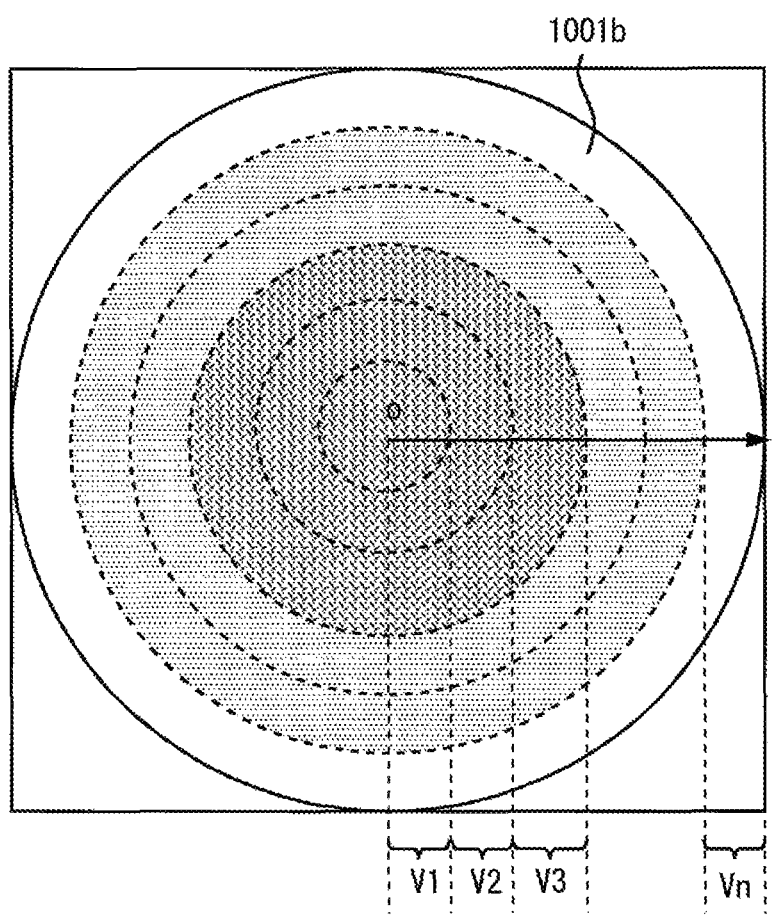
FIG. 25 shows an example of expanding the number of regions in the example of FIG. 24 to N.

Also, although there are three regions in the examples shown in FIGS. 23 and 24, the number is not limited to three and can be extended to n regions as shown in the image 1001b of FIG. 25.

The synthesized image $\xi(V)$ can be expressed in the following formula (8).

[Formula 6]

$$\xi(V)=W(V1)\xi(V1)+W(V2)\xi(V2)+W(V3)\xi(V3)+\ldots+W(Vn)\xi(Vn) \quad (8)$$

According to the fifth embodiment, up-sampled projection data of the number of views V1 to Vn different depending on the distance P from the image center O can be used for synthesizing an image. Therefore, for example, spatial resolution can be increased by a desired amount in the peripheral region from the boundary point $P_0$ by appropriately increasing the number of up-sampling gradually as being farther from the image center O. Hence, spatial resolution can be uniformed over the entire image. Also, images of various qualities can be generated according to the diagnostic purpose by preferentially improving spatial resolution in a desired region.

Although the suitable embodiments of the X-ray CT apparatus related to the present invention are described above, the present invention is not limited to the above embodiments. It is apparent that a person skilled in the art could arrive at various modified examples or amended examples within the scope of the technical ideas disclosed in the present application, and it is understood that these naturally belong to the technical scope of the present invention.

DESCRIPTION OF REFERENCE NUMERALS

1: X-ray CT apparatus
100: scan gantry unit
101: X-ray tube device
102: rotary disk
103: collimator
106: X-ray detector
110: focal shift X-ray controller
120: operation console
121: input device
122: image computing device
123: storage device
124: system controller
125: display device
126: virtual view generation unit
127: reconstruction computing unit
501: FFS (+) projection data
502: FFS (−) projection data
503: FFS projection data (focal shift projection data)
505, 513, 515, 516, and 518: up-sampled projection data

The invention claimed is:

1. An X-ray CT apparatus comprising:
an X-ray tube device that irradiates X-rays to an object from a plurality of focal spots;
an X-ray detector that is disposed oppositely to the X-ray tube device for detecting transmission X-rays transmitted through the object;
a rotary disk that is equipped with the X-ray tube device and the X-ray detector and rotates around the object;
a focal shift X-ray controller that shifts the focal spots in the X-ray tube device to arbitrary positions;
a focal shift projection data generation unit that generates focal shift projection data in combination with the transmission X-rays by each of the irradiated X-rays whose focal spots were shifted to a plurality of positions by the focal shift X-ray controller;
a virtual view generation unit that generates a virtual view in the view direction of the focal shift projection data to generate up-sampled projection data using the virtual view; and
a reconstruction computing unit that reconstructs an image using actual data of the focal shift projection data in a central region closer to the image center than a predetermined boundary in the image plane and using the up-sampled projection data in a peripheral region outside the boundary.

2. The X-ray CT apparatus according to claim 1,
wherein the reconstruction computing unit generates an image in which weighted addition was performed for actual data of the focal shift projection data and up-sampled projection data at a predetermined rate.

3. The X-ray CT apparatus according to claim 2,
wherein the reconstruction computing unit sets a weighting factor used for weighted addition so that spatial resolution of the image continues smoothly in a boundary region including the boundary.

4. The X-ray CT apparatus according to claim 2,
wherein the reconstruction computing unit sets a range where a weighting factor used for weighted addition is changed so as to acquire predetermined spatial resolution in a desired position.

5. The X-ray CT apparatus according to claim 1, further including:
a region-of-interest setting unit that sets a region of interest,
wherein the reconstruction computing unit further uses actual data of the focal shift projection data in a region of interest set by the region-of-interest setting unit.

6. The X-ray CT apparatus according to claim 1,
wherein the virtual view generation unit generates up-sampled projection data of the number of different views, and
the reconstruction computing unit generates an image using up-sampled projection data different in the number of views depending on the distance from the image center in an image plane.

7. The X-ray CT apparatus according to claim 1,
wherein the virtual view generation unit generates focal shift projection data in which the first focal shift projection data acquired by moving the focal spot in the positive direction of the channel direction of the X-ray detector and the second focal shift projection data acquired by moving in the negative direction are alternately combined in the view direction and generates up-sampled projection data by up-sampling the said focal shift projection data in the view direction.

8. The X-ray CT apparatus according to claim 1,
wherein the virtual view generation unit up-samples the first focal shift projection data acquired by moving the focal spot in the positive direction of the channel direction of the X-ray detector and the second focal shift projection data acquired by moving in the negative direction respectively in the view direction and generates up-sampled projection data by alternately combining the up-sampled first and second focal shift projection data in the view direction.

9. The X-ray CT apparatus according to claim 8,
wherein the virtual view generation unit alternately combines the up-sampled first and second focal shift projection data in the view direction to generate projection data and further performs a missing data process for the projection data to generate up-sampled projection data.

10. The X-ray CT apparatus according to claim 8, wherein the virtual view generation unit alternately combines the up-sampled first and second focal shift projection data in the view direction to generate projection data and further up-samples the projection data in the view direction to generate up-sampled projection data.

11. An image reconstruction method including the steps of:
   acquiring focal shift projection data that is projection data by each X-ray irradiated after shifting an X-ray focal spot to a plurality of positions in an X-ray tube device;
   generating a virtual view in the view direction of the focal shift projection data to generate up-sampled projection data using the virtual view; and
   reconstructing an image using actual data of the focal shift projection data in a central region closer to the image center than a predetermined boundary in the image plane and using the up-sampled projection data in a peripheral region outside the boundary.

* * * * *